(12) United States Patent
Ye et al.

(10) Patent No.: US 8,822,384 B2
(45) Date of Patent: Sep. 2, 2014

(54) METHODS FOR DETECTING PLASTICIZERS

(75) Inventors: Bangce Ye, Shanghai (CN); Min Zhang, Shanghai (CN)

(73) Assignee: East China University of Science and Technology, Shanghai (CN)

( * ) Notice: Subject to any disclaimer, the term of this patent is extended or adjusted under 35 U.S.C. 154(b) by 0 days.

(21) Appl. No.: 13/814,610

(22) PCT Filed: Sep. 30, 2011

(86) PCT No.: PCT/CN2011/080456
§ 371 (c)(1),
(2), (4) Date: Feb. 6, 2013

(87) PCT Pub. No.: WO2013/044506
PCT Pub. Date: Apr. 4, 2013

(65) Prior Publication Data
US 2013/0172214 A1     Jul. 4, 2013

(51) Int. Cl.
*G01N 31/22*    (2006.01)
*B82Y 30/00*    (2011.01)
*B82Y 15/00*    (2011.01)

(52) U.S. Cl.
CPC .............. *G01N 31/22* (2013.01); *B82Y 15/00* (2013.01); *Y10S 977/92* (2013.01); *Y10S 977/774* (2013.01); *B82Y 30/00* (2013.01); *Y10S 977/773* (2013.01); *Y10S 977/742* (2013.01)
USPC ................. 506/9; 506/16; 977/920; 977/774; 977/773; 977/742

(58) Field of Classification Search
CPC ........ C40B 30/04; C40B 20/08; G01N 31/22; G01N 31/02; Y10S 977/773; Y10S 977/774; Y10S 977/92
USPC .......................................................... 506/9
See application file for complete search history.

(56) References Cited

U.S. PATENT DOCUMENTS

| | | |
|---|---|---|
| 5,472,881 A | 12/1995 | Beebe et al. |
| 6,750,016 B2 | 6/2004 | Mirkin et al. |
| 7,826,042 B2 * | 11/2010 | Yamamichi et al. ............ 356/72 |
| 2002/0155442 A1 | 10/2002 | Mirkin et al. |
| 2005/0037397 A1 | 2/2005 | Mirkin et al. |
| 2010/0173347 A1 | 7/2010 | Brook et al. |

FOREIGN PATENT DOCUMENTS

| | | |
|---|---|---|
| CN | 101788539 A | 7/2010 |
| CN | 101852766 A | 10/2010 |
| CN | 101858897 A | 10/2010 |

OTHER PUBLICATIONS

Zhang et al., Colorimetric Chiral Recognition of Enantiomers Using the Nucleotide-Capped Silver Nanoparticles, Analytical Chemistry, 2011, 83, 1504-1509.*

Zhang et al., Colorimetric Chiral Recognition of Enantiomers Using the Nucleotide-Capped Siliver Nanoparticles, Analytical Chemistry, 2011, 83, 1504-1509.*

Lomozik et al., Non-Covalent and Coordination Interactions in Cu(II) Systems with Uridine, Uridine-5'-Monophosphate and Triamine or Tetramine as Biogenic Amine Analogs in Aqueous Solutions, Journal of Inorganic Biochemistry, 2003, 97, 179-190.*

Kellett et al., Bis-Phenathroline Copper(II) Phthalate Complexes are Potent in Vitro Antitumor Agents with 'Self-Activating' Metallo-Nuclease and DNA Binding Properties, Dalton Trans., 2011, 40, 1024-1027.*

Botelho et al., Reproductive Effects of Di(2-ethylhexyl)phthalate in Immature Male Rats and Its Relation to Cholesterol, Testosterone, and Thyroxin Levels, A. J. Arch.Environ. Contam. Toxicol., 57(4):777 (2009).

Chatterjee et al., Selective colorimetric sensing of geometrical isomers of dicarboxylates in water by using functionalized gold nanoparticles, Chem. Asian J., 3:1962-1967 (2008).

Choi et al., Aptamer-Capped Nanocrystal Quantum Dots: A New Method for Label-Free Protein Detection, J. Am. Chem. Soc., 128:15584 (2006).

Desvergne et al., PPAR-mediated activity of phthalates: A link to the obesity epidemic? Mol. Cell Endocrinol., 304:43 (2009).

Elghanian et al., Selective colorimetric detection of polynucleotides based on the distance-dependent optical properties of gold nanoparticles, Science, 277:1078 (1997).

Gasowska et al., Specific type of interactions in the quaternary system of Cu(II), adenosine 5'-triphospate, 1,11-diamnio-4,8-diazaundecane and uridine, J. Inorg. Biochem., 101:1362 (2007).

Grabar et al., Preparation and Characterization of Au Colloid Monolayers, Anal. Chem., 67:735-743 (1995).

Huy et al., Multiplexed analysis of silver (I) and mercury (II) ions using oligonucleotide-metal nanoparticle conjugates, Analyst, 136:3289 (2011).

Kellett, et al., Bis-phenanthroline copper (II) phthalate complexes are potent in vitro antitumour agents with 'self-activating' metallo-nuclease and DNA binding properties, Dalton Trans., 40:1024 (2011).

Knobloch et al., Stability and structure of mixed-ligand metal ion complexes that contain $Ni^{2+}$, $Cu^{2+}$, or $Zn^{2+}$, and histamine, as well as adenosine 5'-triphosphate ($ATP^{4-}$) or uridine 5'-triphosphate ($UTP^{4-}$): an intricate network of equilibria, Chemistry, 17:5393 (2011).

Kong et al. Sensitive and Selective Colorimetric Visualization of Cerebral Dopamine Based on Double Molecular Recognition, Angew. Chem. Int. Ed., 50:1837 (2011).

(Continued)

*Primary Examiner* — Maria Leavitt
*Assistant Examiner* — Amy M Bunker
(74) *Attorney, Agent, or Firm* — Knobbe Martens Olson & Bear LLP

(57) ABSTRACT

Nanoparticles having one or more attached sensing moieties including uridine 5'-triphosphate (UTP) and deoxythymidine 5'-triphosphate (dTTP), are disclosed herein. These nanoparticles can, for example, be used for detection of plasticizers, such as phthalates, in the sample. Methods, kits and apparatuses using these nanoparticles for detecting plasticizers in a sample are also disclosed herein.

20 Claims, 16 Drawing Sheets

(56) References Cited

OTHER PUBLICATIONS

Kriss & Yatsimirskii, Reaction of Nucleic Acids with Metals, Russian Chemical Reviews, 35:144 (1966).

Liang et al., A Centrifugation-based Method for Preparation of Gold Nanoparticles and its Application in Biodetection, Int. J. Mol. Sci., 8:526 (2007).

Liu & Lu, A Colorimetric Lead Biosensor Using DNAzyme-Directed Assembly of Gold Nanoparticles, J. Am. Chem. Soc., 125:6642 (2003).

Lomozik & Jastrzab, Non-covalent and coordination interactions in Cu(II) systems with uridine, uridine 5'-monophosphate and triamine or tetramine as biogenic amine analogues in aqueous solutions, J. Inorg. Biochem., 97:179 (2003).

Lopez-Carrillo et al., Exposure to Phthalates and Breast Cancer Risk in Northern Mexico, Environ. Health Perspect., 118:539 (2010).

Scampicchio et al., Optical nanoprobes based on gold nanoparticles for sugar sensing, Nanotechnology, 20:135501 (2009).

Tessier et al., Self-Interaction Nanoparticle Spectoscopy: A Nanoparticle-Based Protein Interaction Assay, J. Am. Chem. Soc., 130:3106 (2008).

Tu & Friederich, Interaction of Copper Ion with Guanosine and Related Compounds, Biochemistry, 7:4367 (1968).

Xue et al., One-Step, Room Temperature, Colorimetric Detection of Mercury ($Hg^{2+}$) Using DNA/Nanoparticle Conjugates, J. Am. Chem. Soc., 130:3244 (2008).

Yang, et al., Carbon Nanotube-Quenched Fluorescent Oligonucleotides: Probes that Fluoresce upon Hybridization, J. Am. Chem. Soc., 130:8351 (2008).

Yang et al., Noncovalent Assembly of Carbon Nanotubes and Single Stranded DNA: An Effective Sensing Platform for Probing Biomolecular Interactions, Anal. Chem., 80:7408 (2008).

Zhang & Ye, Colorimetric Chiral recognition of Enantiomers Using the Nucleotide-Capped Silver Nanoparticles, Anal. Chem., 83:1504 (2011).

Zhang et al., Interaction of peptides with grapheme oxide and its application for real-time monitoring of protease activity, Chem. Commun., 47:2399 (2011).

Zhang et al., A versatile grapheme-based fluorescence "on/off" switch for multiplex detection of various targets, Biosens. Bioelectron., 26:3260 (2011).

Zhang et al., Rapid and sensitive colorimetric visualization of phthalates using UTP-modified gold nanoparticles cross-linked by copper(II), Chem Commun (Camb). 47(43):11849-11851 (2011). doi: 10.1039/c1cc14772b. Epub Oct. 6, 2011.

Zhao et al., Highly Stabilized Nucleotide-Capped Small Gold Nanoparticles with Tunable Size, Adv. Mater., 19:1766 (2007).

Zhao et al., DNA Aptamer Folding on Gold Nanoparticles: From Colloid Chemistry to Biosensors, J. Am. Chem. Soc., 130:3610 (2008).

Zheng, et al., Exposure to di(n-butyl)phthalate and benzo(a)pyrene alters IL-1β secretion and subset expression of testicular macrophages, resulting in decreased testosterone production in rats, Toxicology and Applied Pharmacology, 248(1):28-37 (2010).

International Search Report and Written Opinion dated Jul. 12, 2012 for PCT/CN2011/080456 filed Sep. 30, 2011.

\* cited by examiner

US 8,822,384 B2

METHODS FOR DETECTING PLASTICIZERS

RELATED APPLICATIONS

The instant application is the U.S. National Phase under 35 U.S.C. §371 of International Application No. PCT/CN2011/080456 entitled METHODS FOR DETECTING PLASTICIZERS, filed Sep. 30, 2011, designating the U.S. The content of this application is herein incorporated by reference in its entirety.

BACKGROUND

1. Field

The present disclosure relates to methods for detecting plasticizers, such as phthalates, in a sample. Apparatuses and kits for detecting plasticizers in a sample are also provided in the present disclosure.

2. Description of the Related Art

Plasticizers, for example phthalates, are chemical compounds primarily used in plastics to increase the flexibility, transparency, durability, and longevity of the plastics. For example, a number of phthalates are currently used as plasticizers in food contact packaging material. However, long-term ingestion of various phthalates has been shown to affect hormone balance in humans, which can lead to serious health problems such as confusion of baby gender, decrease of male reproductive ability, and female precocious puberty. Currently available analytical techniques for detecting phthalates in food products include gas chromatography/mass spectroscopy (GC/MS). However, these techniques require expensive and complicated instruments, making on-site and real-time phthalate sensing difficult. There is a need for simple, fast, and low-cost methods for detecting plasticizers in a sample with high selectivity and sensitivity.

SUMMARY

Some embodiments disclosed herein include a method for detecting a plasticizer in a sample, the method comprises: providing a sample suspected of containing a plasticizer; providing a plurality of nanoparticles having one or more attached sensing moieties, wherein the sensing moiety comprises one or more uridine 5'-triphosphate (UTP) groups, uridine 5'-diphosphate (UDP) groups, uridine monophosphate (UMP) groups, 2'-deoxythymidine 5'-triphosphate (dTTP) groups, 2'-deoxythymidine 5'-diphosphate (dTDP) groups, or deoxythymidine 5'-monophosphate (dTMP) groups; contacting the sample with the plurality of nanoparticles in the presence of a crosslinker to form a mixture; maintaining the mixture under conditions allowing the crosslinker to bind the nanoparticles and any plasticizer present in the sample to form a nanoparticle aggregate; and detecting the nanoparticle aggregate.

In some embodiments, the nanoparticles are metallic. In some embodiments, the nanoparticles are gold nanoparticles, silver nanoparticles, platinum nanoparticles, aluminum nanoparticles, palladium nanoparticles, copper nanoparticles, cobalt nanoparticles, indium nanoparticles, nickel nanoparticles, or combinations thereof. In some embodiments, the nanoparticles are gold nanoparticles. In some embodiments, the nanoparticles are gold nanoparticles, silver nanoparticles, quantum dots, carbon nanotubes, graphene oxides, or combinations thereof.

In some embodiments, the nanoparticles have an average diameter of about 12 nm to about 18 nm. In some embodiments, the nanoparticles are present in the mixture at a concentration of about 1 nM to about 20 nM. In some embodiments, the nanoparticles are present in the mixture at a concentration of about 5 nM.

In some embodiments, the sensing moiety comprises one or more UTP groups or dTTP groups. In some embodiments, the sensing moiety comprises one or more UTP groups.

In some embodiments, the crosslinker is $CuCl_2$, $Cu(NO_3)_2$, $CuSO_4$, or combinations thereof. In some embodiments, the crosslinker is $Cu^{2+}$. In some embodiments, the $Cu^{2+}$ is present in the mixture at a concentration of about 0.2 μM to about 0.8 μM. In some embodiments, the $Cu^{2+}$ is present in the mixture at a concentration of about 0.4 μM.

In some embodiments, the plasticizer is a phthalate. In some embodiments, the phthalate is di(2-ethyl-hexyl)phthalate (DEHP), dimethyl phthalate (DMP), di(n-octyl) phthalate (DNOP), diisononyl phthalate (DINP), or combinations thereof.

In some embodiments, the maintaining step is carried out for no more than about 5 minutes. In some embodiments, the maintaining step is carried out at a temperature of about 10° C. to about 40° C.

In some embodiments, the formation of the nanoparticle aggregate results in a colorimetric change. In some embodiments, the colorimetric change is correlated with the concentration of the plasticizer in the sample.

In some embodiments, the detecting step comprises monitoring the difference in absorption spectra of the mixture. In some embodiments, the detecting step comprises monitoring the difference of absorption peak at 520 nm that originates from the surface plasmon absorption of gold nanoparticles. In some embodiments, the detecting step comprises monitoring the decrease in the plasmon absorption at 520 nm and/or the formation of a broadened surface plasmon band around 520-900 nm. In some embodiments, the detecting step comprises determining absorption ratio $A_{610}/A_{520}$ of the mixture. In some embodiments, the detecting step is carried out by an optical sensor. In some embodiments, the detecting step is carried out by visual observation of a user.

In some embodiments, the plasticizer is present in the sample at a concentration of about 0.05 ppM to about 10000 ppM. In some embodiments, the plasticizer is present in the sample at a concentration of about 0.5 ppM to about 100 ppM.

In some embodiments, the sample is a food product or a medicine product.

Some embodiments disclosed herein include an apparatus for detecting a plasticizer in a sample, the apparatus comprises: at least one light source; and a receiver configured to receive at least a portion of the radiation emitted from the light source, wherein the receiver comprises a plurality of nanoparticles and a crosslinker, wherein the nanoparticles have one or more attached sensing moieties, wherein the sensing moiety comprises one or more uridine 5'-triphosphate (UTP) groups, uridine 5'-diphosphate (UDP) groups, uridine monophosphate (UMP) groups, 2'-deoxythymidine 5'-triphosphate (dTTP) groups, 2'-deoxythymidine 5'-diphosphate (dTDP) groups, or deoxythymidine 5'-monophosphate (dTMP) groups.

In some embodiments, the apparatus further comprises at least one light detector configured to measure light emitted from or absorbed by the receiver.

Some embodiments disclosed herein include a kit for detecting a plasticizer in a sample, the kit comprises: a plurality of nanoparticles having one or more attached sensing moieties, wherein the sensing moiety comprises one or more uridine 5'-triphosphate (UTP) groups, uridine 5'-diphosphate (UDP) groups, uridine monophosphate (UMP) groups, 2'-deoxythymidine 5'-triphosphate (dTTP) groups, 2'-deoxythymidine 5'-diphosphate (dTDP) groups, or deoxythymidine 5'-monophosphate (dTMP) groups; and at least one crosslinker that binds the nanoparticles and the plasticizer.

Some embodiments disclosed herein include a nanoparticle aggregate comprising: a plurality of nanoparticles having one or more attached sensing moieties, wherein the sensing moiety comprises one or more uridine 5'-triphosphate (UTP) groups, uridine 5'-diphosphate (UDP) groups, uridine monophosphate (UMP) groups, 2'-deoxythymidine 5'-triphosphate (dTTP) groups, 2'-deoxythymidine 5'-diphosphate (dTDP) groups, or deoxythymidine 5'-monophosphate (dTMP) groups; at least one plasticizer; and at least one crosslinker that binds the nanoparticles to the plasticizer.

In some embodiments, absorption ratio $A_{610}/A_{520}$ of the nanoparticle aggregate is about 0.16 to about 1.2.

In some embodiments, the nanoparticle aggregate is about 30 nm to about 600 nm in diameter. In some embodiments, the nanoparticle aggregate is more than about 600 nm in diameter.

BRIEF DESCRIPTION OF THE DRAWINGS

FIG. 1 is a schematic representation illustrating an embodiment of the method for detecting plasticizers using nanoparticles having one or more sensing moieties that is within the scope of the present disclosure.

FIG. 9 shows the UV-vis absorbance of the UTP-AuNPs in solution upon addition of varied concentration of DEHP (0, 0.5, 1, 10, 50, 100, 1000, 5000, and 10000 ppm) in the presence of 0.4 µM $Cu^{2+}$ acting as cross-linkers.

FIG. 10 shows the UV-vis absorbance of the UTP-AuNPs in solution upon addition of various phthalates (10 g/L of DMP, DNOP and DEHP) and control analytes (10 g/L ethyl benzoate, phthalate acid, sodium oxalate and sodium citrate) in the presence of 0.4 µM $Cu^{2+}$ acting as cross-linkers.

FIG. 11 shows the detection of DEHP in food samples tainted with DEHP.

DETAILED DESCRIPTION

Figure 1A:
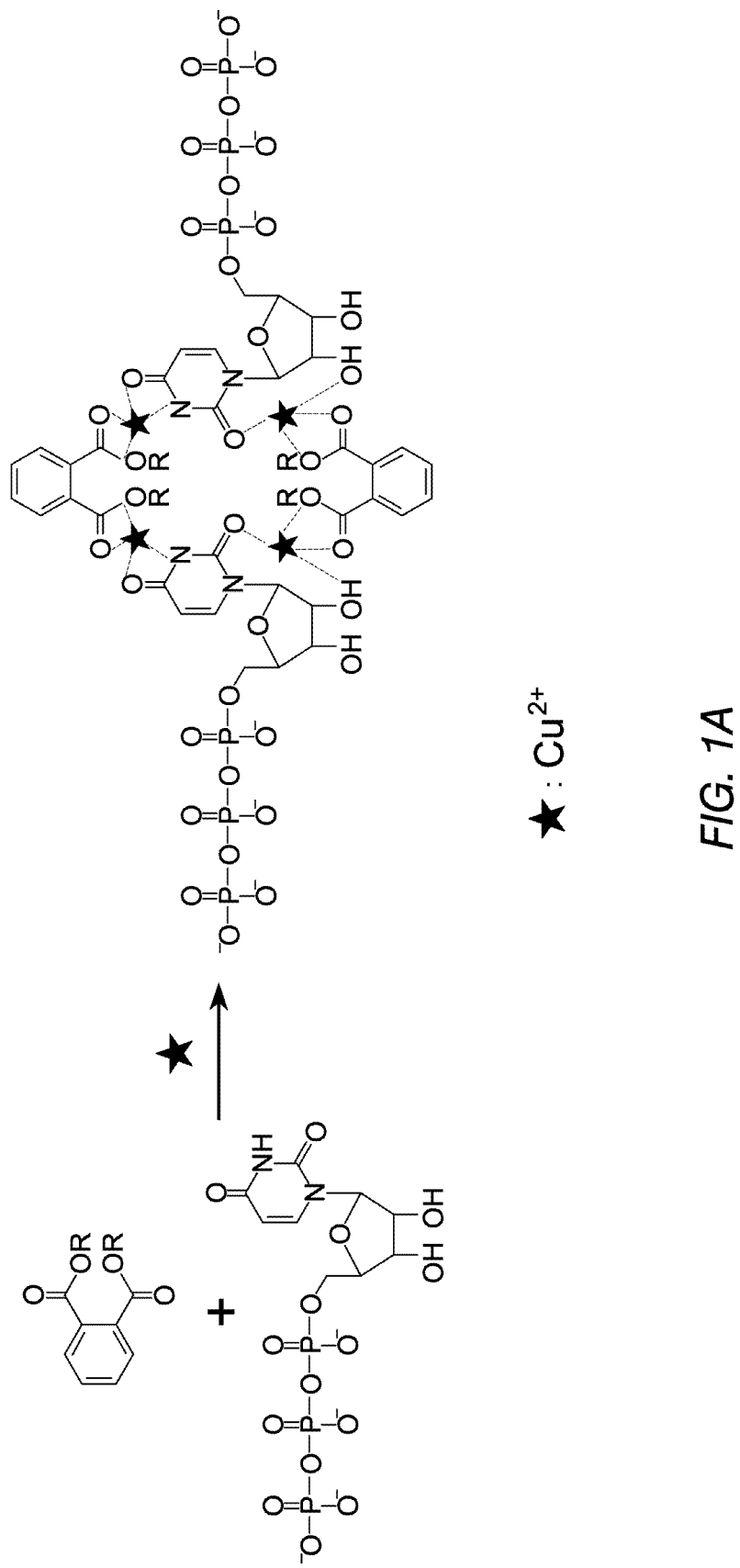
FIG. 1A depicts an exemplary $Cu^{2+}$-induced cross-linking recognition between uridine 5'-triphosphate (UTP) and phthalates.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Definitions

As used herein, the term "nanoparticle" refers to a small piece of matter that can be composed of metals and/or non-metallic materials. A "nanoparticle" can be in any shape, such as spherical or rod-shaped, and which is typically of about 0.1 nm to about 200 nm in diameter.

As used herein, the term "nucleotide" refers to a chemical compound that consists of a heterocyclic base (e.g., adenine, guanine, cytosine, uracil and thymine), a five-carbon sugar (deoxyribose or ribose), and one or more phosphate groups. A nucleotide can be a ribonucleotide or a deoxyribonucleotide. The term "oligonucleotide" refers to a short nucleic acid sequence having typically twenty or fewer nucleotides. In some embodiments, the nucleotides or the oligonucleotides can be functionalized.

As used herein, the term "sensing moiety" refers to a chemical or biochemical molecule or fragment thereof that is capable of interacting or binding specifically with an analyte of interest, for example a plasticizer, in a sample. The interaction and/or the binding between the sensing moiety and the analyte of interest can be direct or indirect. In some embodiments, the sensing moiety binds to the analyte of interest through crosslinking by a crosslinker. In some embodiments, the binding between the sensing moiety and the analyte provide one or more detectable signals. Non-limiting examples of sensing moiety include nucleotides and oligonucleotides.

As used herein, the term "aggregation" refers to the association of nanoparticles, for example, gold nanoparticles (AuNPs). In some embodiments, the inter-nanoparticle association is induced by the crosslinking of the nanoparticles and the plasticizers present in a sample through crosslinkers.

Disclosed in the present disclosure are methods for detecting plasticizers, such as phthalates, in a sample. Also disclose herein are nanoparticles having one or more attached sensing moieties. As described herein, aggregation of the nanoparticles having one or more attached sensing moieties can be selectively induced by plasticizers in the presence of crosslinkers, such as copper (II) salts.

In some embodiments, the methods for detecting plasticizers include providing a sample suspected of containing a plasticizer, providing a plurality of the nanoparticles having one or more attached sensing moieties, contacting the sample with the plurality of the nanaoparticles in the presence of a crosslinker to form a mixture, maintaining the mixture under conditions allowing the crosslinker to bind the nanoparticles and any plasticizer present in the sample to form a nanoparticle aggregate; and detecting the nanoparticle aggregate. The present disclosure also relates to apparatuses and kits for detecting plasticizers in a sample using the nanoparticles having one or more attached sensing moieties.

Nanoparticles Having Attached Sensing Moieties

The present disclosure relates to the use of any suitable nanoparticles having one or more sensing moieties attached thereto that are suitable for use in detection assays.

Because of their unique structural and photophysical features, nanoparticles have been studied widely for their applications in chemical and biochemical assays. Nanoparticles can be made of various materials, including metals, non-metallic materials, and any combinations thereof. Non-limiting examples of nanoparticles include gold nanoparticles, silver nanoparticles, platinum nanoparticles, aluminum nanoparticles, palladium nanoparticles, copper nanoparticles, cobalt nanoparticles, indium nanoparticles, nickel nanoparticles, quantum dots, carbon nanotubes, graphene oxides, and any combinations thereof. In some embodiments, the nanoparticle is a gold nanoparticle (AuNP).

The nanoparticles suitable for use in the methods, kits and apparatuses disclosed herein can be of various sizes. In some embodiments, the nanoparticle has a diameter of about 0.1 nm to about 200 nm, about 0.5 nm to about 100 nm, about 1 nm to about 50 nm, about 2 nm to about 10 nm, or about 2 nm to about 5 nm. In some embodiments, the nanoparticle has a diameter of about 0.5 nm, about 1 nm, about 2 nm, about 3 nm, about 4 nm, about 5 nm, about 6 nm, about 7 nm, about 8 nm, about 9 nm, about 10 nm, about 11 nm, about 12 nm, about 13 nm, about 14 nm, about 15 nm, about 16 nm, about 17 nm, about 18 nm, about 19 nm, about 20 nm, about 30 nm, about 50 nm, about 80 nm, about 100 nm, about 110 nm, or a range between any two of these values. In some embodiments, the nanoparticle has a diameter of about 12-18 nm. In some embodiments, the nanoparticle has a diameter of about 15 nm.

As disclosed herein, the nanoparticle can have one or more sensing moieties attached thereto. In some embodiments, the nanoparticle have about 1, about 2, about 3, about 4, about 5, about 6, about 7, about 8, about 9, about 10, about 15, about 20 sensing moieties attached thereto. In some embodiments, the sensing moiety comprises one or more nucleotides. In some embodiments, the sensing moiety comprises about 1, about 2, about 3, about 4, about 5, about 6, about 7, about 8, about 9, about 10, about 15, about 20 nucleotides. In some embodiments, the sensing moiety is a nucleotide. In some embodiments, the sensing moiety is an oligonucleotide.

As disclosed herein, the sensing moiety can include various types of nucleotides. Examples of the nucleotide include, but are not limited to, uridine 5'-triphosphate (UTP), uridine 5'-diphosphate (UDP), uridine monophosphate (UMP), 2'-deoxythymidine 5'-triphosphate (dTTP), 2'-deoxythymidine 5'-diphosphate (dTDP), and deoxythymidine 5'-monophosphate (dTMP). In some embodiments, the nucleotide is UTP or dTTP. In some embodiments, the nucleotide is UTP. In some embodiments, the sensing moiety is UTP group. A skilled artisan can readily appreciate that other molecules which contain the nucleotides can behave analogously to the nucleotides. For example, in some embodiments, an oligonucleotide having 20 or fewer nucleotides is attached to the nanoparticle, where the oligonucleotide includes at least one or more UTP, UDP, UMP, dTTP, dTDP, or dTMP. As disclosed herein, the oligonucleotide can have about 20, about 19, about 18, about 17, about 16, about 15, about 14, about 13, about 12, about 11, about 10, about 9, about 8, about 7, about 6, about 5, about 4, about 3, about 2 nucleotides, or a range between any two of these values. In some embodiments, the oligonucleotide is a DNA or RNA oligonucleotide. In some embodiments, the oligonucleotide is a DNA-RNA hybrid oligonucleotide.

The sensing moieties, for example nucleotides or oligonucleotides, can be attached to the nanoparticles using any suitable methods known in the art. For example, nucleotides and/or oligonucleotides can be attached to metal nanoparticles through nucleobases and/or the phosphodiester backbone (see, e.g., Blackburn & Gait, Nucleic Acids in Chemistry and Biology, Oxford University Press, Oxford, UK, 1990). In some embodiments, the sensing moiety comprises one or more nucleotides and the nanoparticle is metallic, wherein the sensing moiety is attached to the nanoparticle through the interaction between the nucleobase(s) and/or the phosphate(s) of the nucleotides and the metal surface of the nanoparticle. The nanoparticles, the nucleotides (or the oligonucleotides), or both can also be functionalized in order to attach the nucleotides (or the oligonucleotides) to the nanoparticles. For example, oligonucleotides having an alkanethiol, an alkanedisulfide, or a cyclic disulfide covalently bound to their 5'-termini or 3'-termini can be used to bind the oligonucleotides to a variety of nanoparticles, including gold nanoparticles. Methods of attaching oligonucleotides to nanoparticles are further described in U.S. Patent Publication US2005-0037397 A1. The oligonucleotides can also be attached to the nanoparticles using sulfur-based functional groups. U.S. Pat. No. 6,750,016 and U.S. Patent Publication No. 2002-0155442 A1 describe that oligonucleotides functionalized with a cyclic disulfide can be readily attached to nanoparticles. The cyclic disulfides preferably have 5 or 6 atoms in their rings, including the two sulfur atoms. Suitable cyclic disulfides are available commercially or may be synthesized by known procedures. The reduced form of the cyclic disulfides can also be used. Other functional groups for attaching oligonucleotides to solid surfaces include phosphorothioate groups (see, e.g., U.S. Pat.

No. 5,472,881 for the binding of oligonucleotide-phosphorothioates to gold surfaces). In some embodiments, the nanoparticle is amino-functionalized for the sensing moiety to attach to.

Methods for Detecting Plasticizers

Some embodiments of the present disclosure include methods for detecting plasticizers, such as phthalates, in a sample. In some embodiments, the method include providing a sample suspected of containing a plasticizer and a plurality of the nanoparticles having one or more attached sensing moieties, contacting the sample with the plurality of the nanoparticles in the presence of a crosslinker to form a mixture, maintaining the mixture under conditions allowing the crosslinker to bind the nanoparticles and any plasticizer present in the sample to form a nanoparticle aggregate, and detecting the nanoparticle aggregate.

As used herein, the term "crosslinker" refers to a chemical compound that can crosslink a nanoparticle having one or more attached sensing moieties as disclosed herein and any plasticizer. Non-limiting examples of crosslinker include various copper salts, such as $CuCl_2$, $Cu(NO_3)_2$, $CuSO_4$, and any combinations thereof. In some embodiments, the crosslinker is $Cu^{2+}$. In some embodiments, the crosslinker can interact with the sensing moieties, for example nucleotides or oligonucleotides, attached on the nanoparticles. The concentration of the crosslinkers effective for crosslinking the nanoparticles and the phthalates can vary. For example, the effective concentration of the crosslinker can be about 0.2 µM, about 0.3 µM, about 0.4 µM, about 0.5 µM, about 0.6 µM, about 0.7 µM, about 0.8 µM, or ranges between any two of these values. In some embodiments, the effective concentration of the crosslinker is about 0.2 µM to about 0.8 µM. In some embodiments, the effective concentration of the crosslinker is about 0.4 µM.

The sample suspected of containing a phthalate is, in some embodiments, contacted with the plurality of the nanoparticles in the presence of the crosslinker to form a mixture. The concentration of the crosslinker in the mixture can vary. In some embodiments, the crosslinker is present in the mixture at a concentration from about 0.2 µM to about 0.8 µM. In some embodiments, the crosslinker is present in the mixture at a concentration of about 0.4 µM.

The nanoparticles can also be present in the mixture at various concentrations. In some embodiments, the nanoparticles are present in the mixture at a concentration of about 1 nM, about 2 nM, about 3 nM, about 4 nM, about 5 nM, about 6 nM, about 7 nM, about 8 nM, about 9 nM, about 10 nM, about 12 nM, about 15 nM, about 20 nM, or ranges between any two of these values. In some embodiments, the nanoparticles are present in the mixture at a concentration of about 1 nM to about 20 nM. In some embodiments, the nanoparticles are present in the mixture at a concentration of about 5 nM.

Methods, apparatuses and kits disclosed herein can be used to detect various plasticizers in a sample. Non-limiting examples of plasticizer include phthalate-based plasticizers, for example 1,2-benzenedicarboxylic acid esters. Examples of phthalate-based plasticizers include, but are not limited to, di(2-ethylhexyl)phthalate (DEHP), diisononyl phthalate (DINP), di-n-butyl phthalate (DBP), benzyl butyl phthalate (BBP), diisodecyl phthalate (DIDP), di(n-octyl) phthalate (DNOP), diisooctyl phthalate (DIOP), diethyl phthalate (DEP), diisobutyl phthalate (DIBP), dimethyl phthalate (DMP), diallyl phthalate (DAP), di-n-propyl phthalate (DPP), butyl cyclohexyl phthalate (BCP), di-n-pentyl phthalate (DNPP), dicyclohexyl phthalate (DCP), di-n-hexyl phthalate (DNHP), diisohexyl phthalate (DIHxP), diisoheptyl phthalate (DIHpP), butyl decyl phthalate (BDP), n-Octyl n-decyl phthalate (ODP), di(2-Propyl Heptyl) phthalate (DPHP), diundecyl phthalate (DUP), diisoundecyl phthalate (DIUP), diisoundecyl phthalate (DTDP), diisotridecyl phthalate (DIUP), and any combination thereof. In some embodiments, the plasticizer is DEHP, DMP, DNOP, DINP, or combinations thereof. In some embodiments, the plasticizer is DEHP.

Figure 1B:
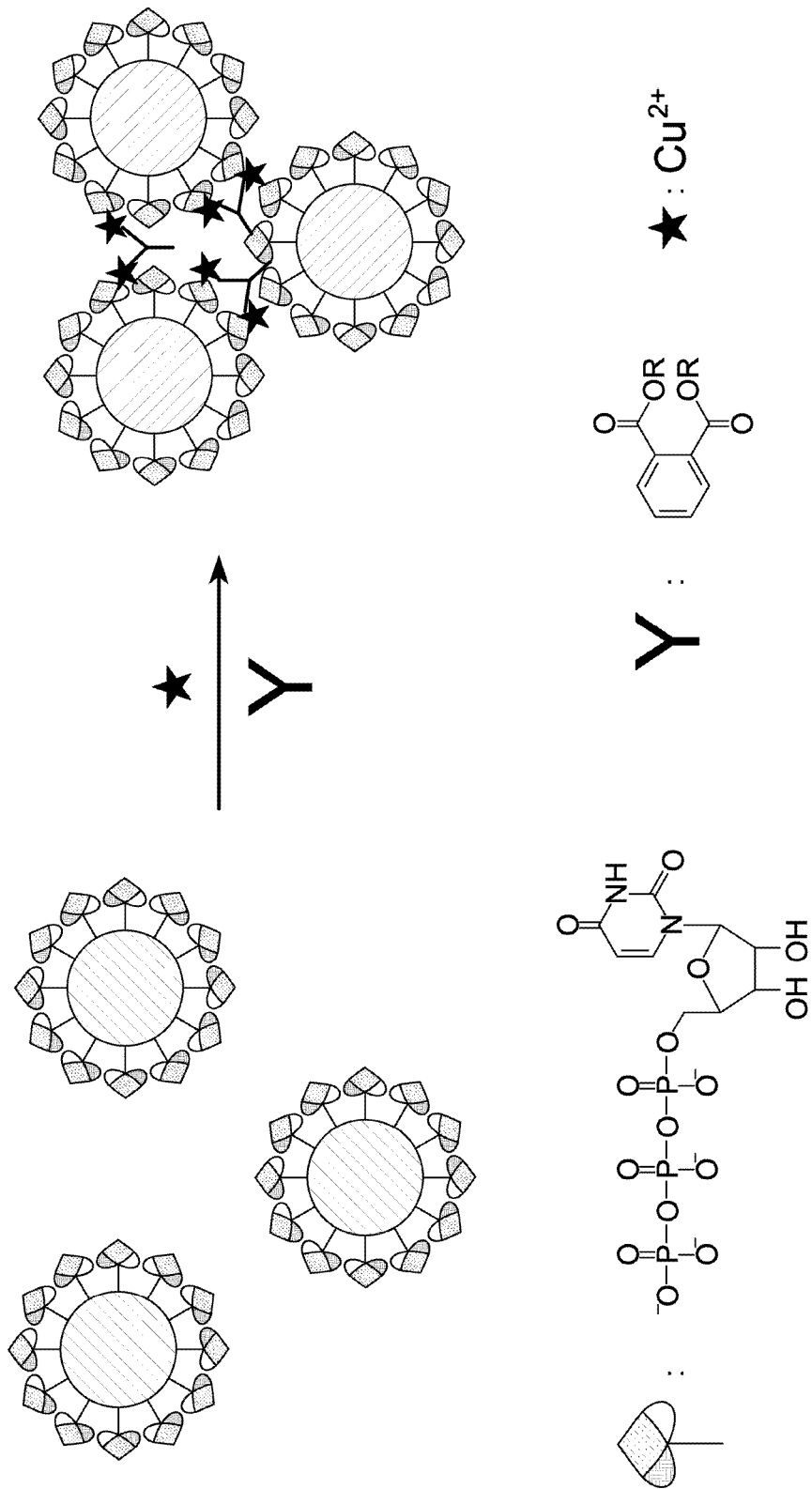
FIG. 1B is a schematic diagram illustrating colorimetric detection of phthalates using UTP-modified gold nanoparticles (UTP-AuNPs).

The methods disclosed in the present disclosure can selectively detect plasticizers, such as phthalates. As schematically illustrated in FIG. 1, in some embodiments, the cross-linking of plasticizers (e.g., phthalates) and the sensing moiety (e.g., UTP) attached on the nanoparticles by the crosslinker (e.g., $Cu^{2+}$) can induce aggregation of the nanoparticles, and thus form a nanoparticle aggregate. In some embodiments, the size of the nanoparticle aggregate is correlated with the concentration of phthalates in the sample. In some embodiments, the size of the nanoparticle aggregate increases with an increase in the concentration of phthalates in the sample.

As disclosed herein, the nanoparticle aggregate can include a plurality of nanoparticles having one or more sensing moieties, at least one plasticizer, and at least one crosslinker that binds the nanoparticles to the plasticizer. The size of the nanoparticle aggregate can vary. For example, the diameter of the nanoparticle aggregate can be about 20 nm, about 30 nm, about 50 nm, about 100 nm, about 200 nm, about 300 nm, about 400 nm, about 500 nm, about 600 nm, about 700 nm, about 800 nm, about 900 nm, about 1000 nm, or a range between any two of these values. In some embodiments, the diameter of the nanoparticle aggregate is at least about 30 nm, at least about 100 nm, at least about 200 nm, at least about 300 nm, at least about 400 nm, at least about 500 nm, at least about 600 nm, at least about 700 nm, or at least about 800 nm. In some embodiments, the diameter of the nanoparticle aggregate is about 30 nm to about 600 nm. In some embodiments, the diameter of the nanoparticle aggregate is more than 600 nm. The absorption ratio $A_{610}/A_{520}$ of the nanoparticle aggregate can be about 0.16, about 0.36, about 0.56, about 0.76, about 0.96, or about 1.16, or ranges between any two of these values. In some embodiments, the absorption ratio $A_{610}/A_{520}$ of the nanoparticle aggregate is about 0.16 to about 0.48. In some embodiments, the absorption ratio $A_{610}/A_{520}$ of the nanoparticle aggregate is about 0.16 to about 0.96.

The nanoparticle aggregate can be detected using any means known in the art. In some embodiments, the formation of the nanoparticles aggregates causes the mixture of the nanoparticles, plasticizers and crosslinker to produce a color change, which thus allows colorimetric detection of the plasticizers. The colorimetric change of the mixture can be readily detected using any means known in the art, for example, be detected by an optical sensor or by visual observation of a user. In some embodiments, the detection of nanoparticle aggregate is carried out by an optical sensor. In some embodiments, the detection of nanoparticle aggregate is carried out by a spectrophotometer. In some embodiments, the detection of nanoparticle aggregate is carried out by visual observation of a user. In some embodiments, the detection of nanoparticle aggregate is carried out by determining absorption ration $A_{610}/A_{520}$ of the mixture.

The methods disclosed in the present disclosure can be used to detect the presence of plasticizers, such as phthalates, as well as to measure the concentration of the plasticizers in a sample. In some embodiments, the amount of the nanoparticle aggregate is correlated with the concentration of the plasticizer in the sample. In some embodiments, the colorimetric change is correlated with the concentration of the plasticizers in the sample. In some embodiments, the response of the nanoparticles to the presence of the plasticizer and/or the concentration (or the change in concentration) of the plasticizer, is converted into a detectable signal. In some embodiments, the detectable signal is an optical signal, such as a color change of the mixture. In some embodiments, the color change is detectable by naked eye observation of a user or an optical sensor. In some embodiments, the optical signal is detected by an ultraviolet-visible spectrophotometer.

In some embodiments of the methods disclosed herein, the mixture of the nanoparticles, crosslinker and sample can be maintained under conditions allowing the crosslinker to bind the nanoparticles and any plasticizer present in the sample to form the nanoparticle aggregate. The mixture can be maintained at about 10° C., about 11° C., about 12° C., about 13° C., about 14° C., about 15° C., about 16° C., about 17° C., about 18° C., about 19° C., about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., or ranges between any two of these values for allowing the formation of the nanoparticle aggregate. In some embodiments, the mixture is maintained at about 10° C. to about 40° C. In some embodiments, the mixture is maintained at about 25° C. to about 33° C. In some embodiments, the mixture is maintained at about room temperature.

The time period for which the mixture is maintained to allow the formation of the nanoparticle aggregate can vary. For example, the mixture can be maintained for about 5 seconds, about 30 seconds, about 1 minute, about 5 minutes, about 10 minutes, about 15 minutes, about 20 minutes, about 25 minutes, about 30 minutes, about 45 minutes, about 1 hour, about 2 hours, about 3 hours, about 4 hours, about 5 hours, about 6 hours, or ranges between any two of these values to allow the crosslinker to bind the nanoparticles to the plasticizer to form the nanoparticle aggregate. In some embodiments, the mixture is maintained for no more than about 6 hours, no more than about 5 hours, no more than about 4 hours, no more than about 3 hours, no more than about 2 hours, no more than about 1 hour, no more than about 45 minutes, no more than about 30 minutes, no more than about 15 minutes, no more than about 5 minutes, or no more than about 1 minute to form the nanoparticle aggregate. In some embodiments, the mixture is maintained for no more than about 5 minutes.

The methods described herein can allow rapid detection of plasticizers in a sample. For example, the minimal time needed for the sample to contact with the nanoparticles to allow detection of the plasticizer and/or measuring of the concentration of the plasticizer can be about 60 minutes, about 50 minutes, about 40 minutes, about 30 minutes, about 20 minutes, about 10 minutes, about 5 minutes, about 4 minute, about 3 minutes, about 2 minutes, about 1 minutes, about 30 seconds, about 12 seconds, about 6 seconds, or shorter. In some embodiments, the minimal time needed for the sample to contact with the nanoparticles to allow detection of the plasticizer and/or measuring of the concentration of the plasticizer is at most about 1 second, at most about 3 seconds, at most about 6 seconds, at most about 9 seconds, at most about 12 seconds, at most about 18 seconds, at most about 24 seconds, at most about 30 seconds, at most about 1 minute, at most about 5 minutes, at most about 10 minutes, at most about 15 minutes, at most about 20 minutes, at most 25 minutes, or at most 30 minutes.

The methods described herein allow detection of plasticizers, such as phthalates, in a wide range of concentrations, including very low concentrations. For example, the concentration of the plasticizer in the sample can be about 0.05 ppm to about 10000 ppm, about 0.1 ppm to about 1000 ppm, about 0.5 ppm to about 100 ppm, about 1 ppm to about 10 ppm, about 1 ppm to about 5 ppm, and about 1 ppm to about 3 ppm. The concentration of the plasticizer in the sample can be about 0.01 ppm, about 0.05 ppm, about 0.5 ppm, about 0.6 ppm, about 0.7 ppm, about 0.8 ppm, about 0.9 ppm, about 1 ppm, about 1.1 ppm, about 1.2 ppm, about 1.3 ppm, about 1.4 ppm, about 1.5 ppm, about 1.6 ppm, about 1.7 ppm, about 1.8 ppm, about 1.9 ppm, about 2 ppm, about 5 ppm, about 10 ppm, about 20 ppm, about 30 ppm, about 40 ppm, about 50 ppm, about 100 ppm, about 500 ppm, about 1000 ppm, about 5000 ppm, about 10000 ppm, and ranges between any two of these values. In some embodiments, the concentration of the plasticizer in the sample is less than about 100 ppm. In some embodiments, the concentration of the plasticizer in the sample is less than about 10 ppm. In some embodiments, the concentration of the plasticizer in the sample is less than about 5 ppm. In some embodiments, the concentration of the plasticizer in the sample is less than about 2 ppm. In some embodiments, the concentration of the plasticizer in the sample is less than about 1.5 ppm. In some embodiments, the concentration of the plasticizer in the sample is less than about 1 ppm. In some embodiments, the concentration of the plasticizer in the sample is about 0.5 ppm.

The methods described herein can be used for detecting plasticizers, such as phthalates, in various types of samples. In some embodiments, the sample can be an environmental sample, a food product, a medicine product, a dietary supplement, a dental hygienic composition, a cosmetic product, or a biological sample. In some embodiments, the sample is an aqueous sample. In some embodiments, the food product is a beverage. In some embodiments, the food product contains liquid or powder milk, tea, juice, or coffee. In some embodiments, the beverage is water, carbonated water, carbonated soda, baby formula, electrolyte drinks, protein drinks, fruit smoothies, or fruit juice.

Apparatuses for Detecting Plasticizers

Some embodiments of the present disclosure include apparatuses for detecting plasticizer, such as phthalates, in a sample. In some embodiments, the apparatus includes: at least one light source; and a receiver configured to receive at least a portion of the radiation emitted from the light source, wherein the receiver comprises a plurality of nanoparticles having one or more attached sensing moieties. In some embodiments, the light source provides an intensity and wavelength sufficient to excite the nanoparticles. Suitable light sources are known to those of skill in the art and are commercially available.

In some embodiments, the apparatus further comprises at least one light detector configured to measure light emitted from or absorbed by the receiver. In some embodiments, the light source is configured to emit an ultraviolet or violet radiation. In some embodiments, the apparatus further comprises a housing, wherein the housing contains the plurality of the nanoparticles and is configured to receive a sample adjacent to the plurality of the nanoparticles. For example, the plurality of the nanoparticles can be exposed to the light source such as a laser at a preset angle of incidence before, during, and/or after contacting the plurality of the nanoparticles with a sample suspected of containing the plasticizer in the presence of the crosslinker. In some embodiments, a change in the absorption spectra of the nanoparticles indicates binding of the plasticizer to the nanoparticles. The light detector can be an optical sensor adapted to detected light emitted from the nanoparticles.

Figure 2:
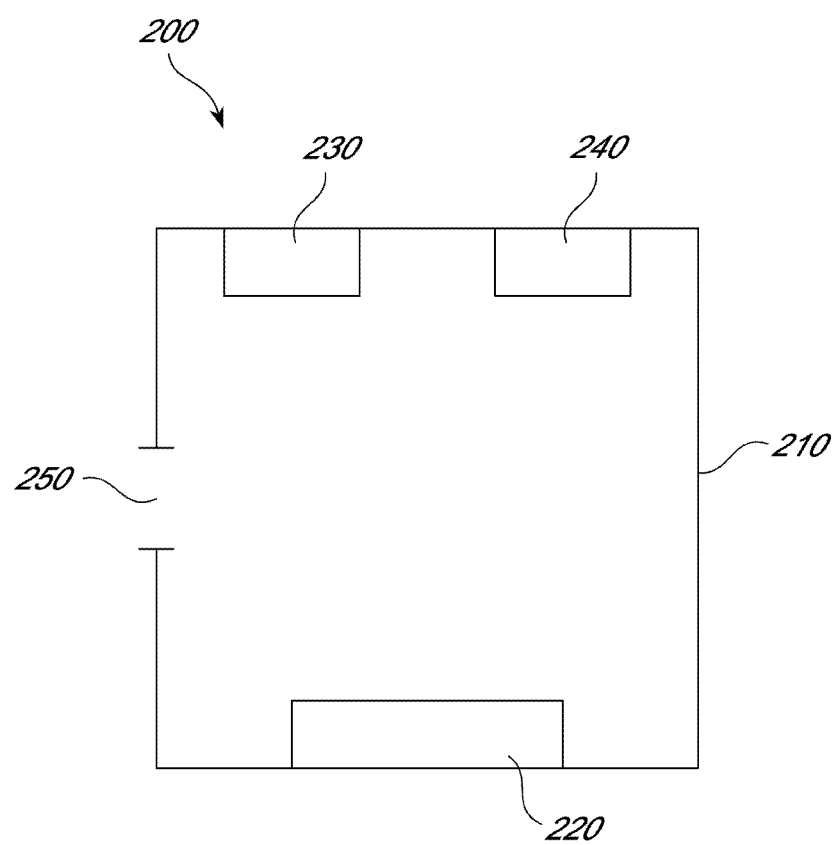
FIG. 2 depicts an illustrative embodiment of an apparatus for detecting plasticizers that is within the scope of the present disclosure (not to scale).

FIG. 2 depicts an illustrative embodiment of an apparatus for detecting a plasticizer that is within the scope of the present disclosure. Apparatus 200 can include housing 210 that contains a solution of nanoparticles 220, light source 230, light detector 240, and port 250. Light source 230 is configured to emit radiation effective to produce fluorescence from nanoparticle solution 220. For example, light source 230 can be an InGaN semiconductor that emits blue or ultraviolet radiation. Light detector 240 can be configured to measure light emission from or light adsorption by nanoparticle solution 220. Port 250 can be configured to receive a sample into the housing. Thus, for example, a sample suspected of containing one or more target molecules, such as plasticizers, can be placed into housing 210 via port 250, so that the sample contacts nanoparticle solution 220. Light source 230 can then emit light and the absorption by or reflectance from nanoparticle solution 220 is detected by light detector 240. The amount of the absorption or reflectance can then be correlated with the presence of the phasticizer, such as the phthalate, in the sample.

Apparatuses for Detecting Plasticizers

Some embodiments of the present disclosure also provide kits for detecting plasticizers in a sample. In some embodiments, the kit includes a plurality of nanoparticles having one or more attached sensing moieties, and at least one crosslinker that binds the nanoparticles and the plasticizer. In some embodiments, the sensing moiety comprises one or more UTP groups, UDP groups, UMP groups, dTTP groups, dTDP groups, or dTMP groups. In some embodiments, the sensing moiety comprises one or more UTP groups.

In some embodiments, the kit includes a high-throughput microplate containing an array of wells, where each well having the same or different solution of specific nanoparticles and crosslinkers to detect plasticizers. In some embodiments, an aliquot of the sample can be mixed with each well in the array, thereby allowing the assay to be performed in parallel wells.

EXAMPLES

Additional embodiments are disclosed in further detail in the following examples, which are not in any way intended to limit the scope of the claims.

Example 1

Preparation of Nucleotide-Modified Gold Nanoparticles

All glassware was thoroughly cleaned overnight with freshly prepared 3:1 HCl/HNO$_3$ (aqua regia) and rinsed thoroughly with Mill-Q water prior to use. Citrate-stabilized gold nanoparticles (AuNPs) were prepared according to the method described in Grabar et al., Int. J. Mol. Sci., 8: 526 (2007). Briefly, 100 mL of HAuCl$_4$ (0.01%) was added to a 250 mL round bottle and then boiled. Under rapid stirring, 3.5 mL of trisodium citrate (1%) was added and further rapidly stirred for 15 minutes. After stirred for 30 minutes, the solution was then gradually cooled to room temperature, and was filtered by 0.22 μm filter paper, which was stored in the refrigerator (4° C.) before further use.

For the surface modification of AuNPs with mononucleotides, an aliquot of 30 μL (2.0 mM) uridine 5'-triphosphate (UTP), 2'-deoxyadenosine triphosphate (dATP), 2'-deoxyguanosine triphosphate (dGTP), 2'-deoxycytidine triphosphate (dCTP), 2'-deoxythymidine triphosphate (dTTP), adenosine 5'-triphosphate (ATP), guanosine 5'-triphosphate (GTP), or cytidine 5'-triphosphate (CTP) was added to 970 μL of AuNPs colloidal solutions. After incubating for 3 hours at 4° C., the resulting mixture was subject to centrifugation at the speed of 12000 rpm for 30 minutes. The supernatant fluid was removed, while the AuNPs precipitate was dissolved with 200 μL Mili-Q water. The resulting mononucleotide-modified AuNPs solutions were stored in the refrigerator (at 4° C.) for further use.

Without being bound with any particular theory, it is believed that the nucleotides can bind to the surface of the gold nanoparticles, due to the interaction between functional groups (e.g., amines, carbonyls) of the nucleobases and the metal surface, and the negatively charged phosphate group along the phosphodiester backbone can stabilize the nanoparticles against aggregation via electrostatic repulsion.

Example 2

Physical and Optical Properties of UTP-Modified AuNPs

UTP-modified gold nanoparticles (UTP-AuNPs) were prepared according to the procedure described in Example 1. The as-prepared UTP-AuNPs were red in color and showed a characteristic absorption peak at 520 nm, which was ascribed to the surface plasmon resonance of the AuNPs. Without being bound to any particular theory, it is believed that the U-AuNPs solution can be highly stabilized against aggregation due to the negative UTP's electrostatic repulsion between AuNPs.

Figure 3A:
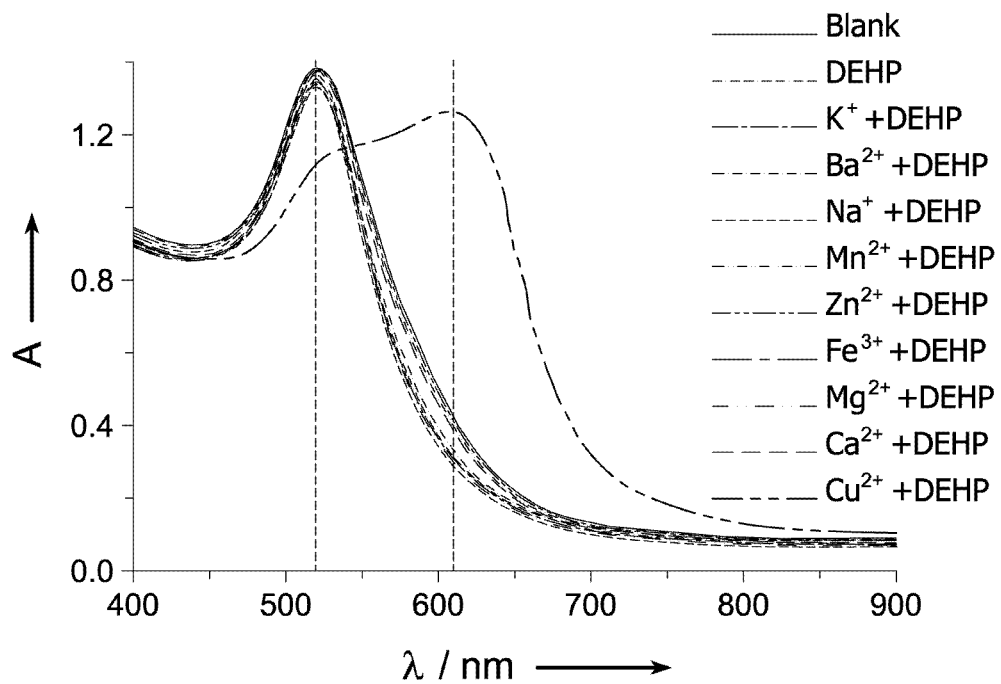
FIG. 3A shows the typical absorption spectra of the UTP-AuNPs in the absence or presence of phthalates upon the simultaneous presence of various metal ions including 0.4 µM $K^+$, $Ba^{2+}$, $Na^+$, $Mn^{2+}$, $Zn^{2+}$, $Fe^{3+}$, $Mg^{2+}$, $Ca^{2+}$, and $Cu^{2+}$.
Figure 3B:
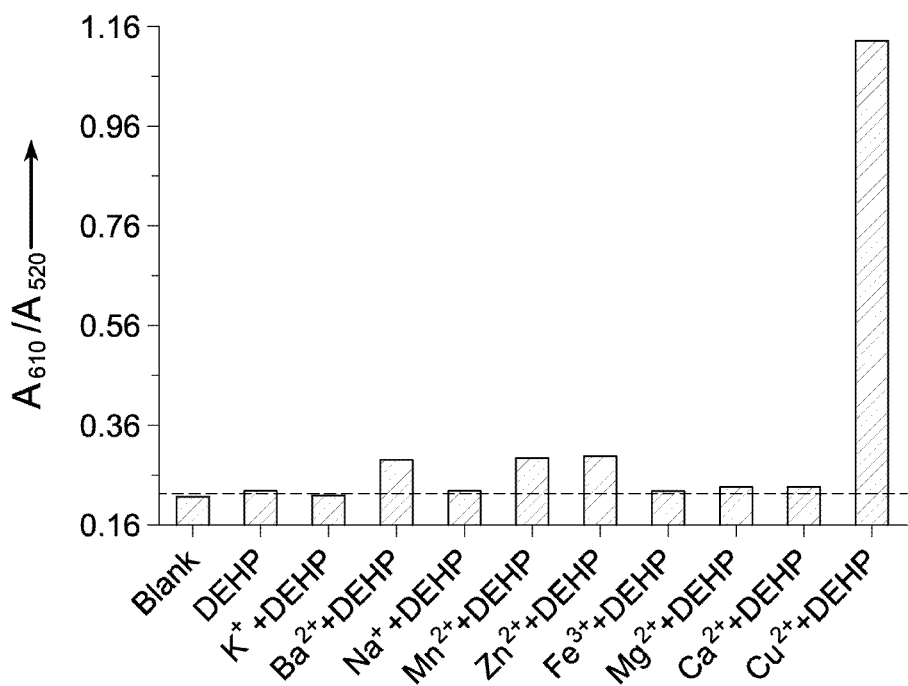
FIG. 3B shows the absorption ratio ($A_{610}/A_{520}$) of the UTP-AuNPs in the absence or presence of phthalates upon the simultaneous addition of various metal ions indicated.
Figure 3C:
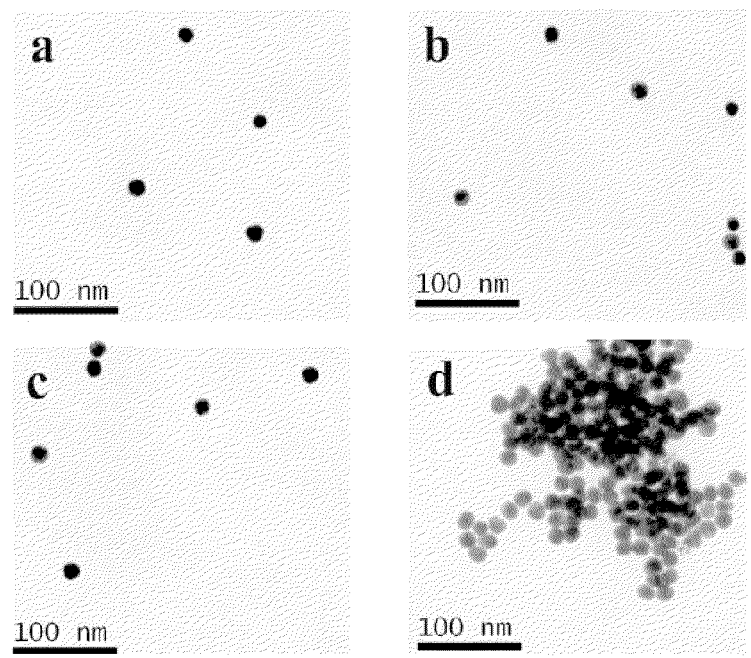
FIG. 3C shows the TEM images of UTP-AuNPs (image a) and the U-AuNPs in the presence of 0.4 µM $Cu^{2+}$ (image b), 10 g/L phthalates (image c), and 0.4 µM $Cu^{2+}$+10 g/L phthalates (image d).
Figure 4A:
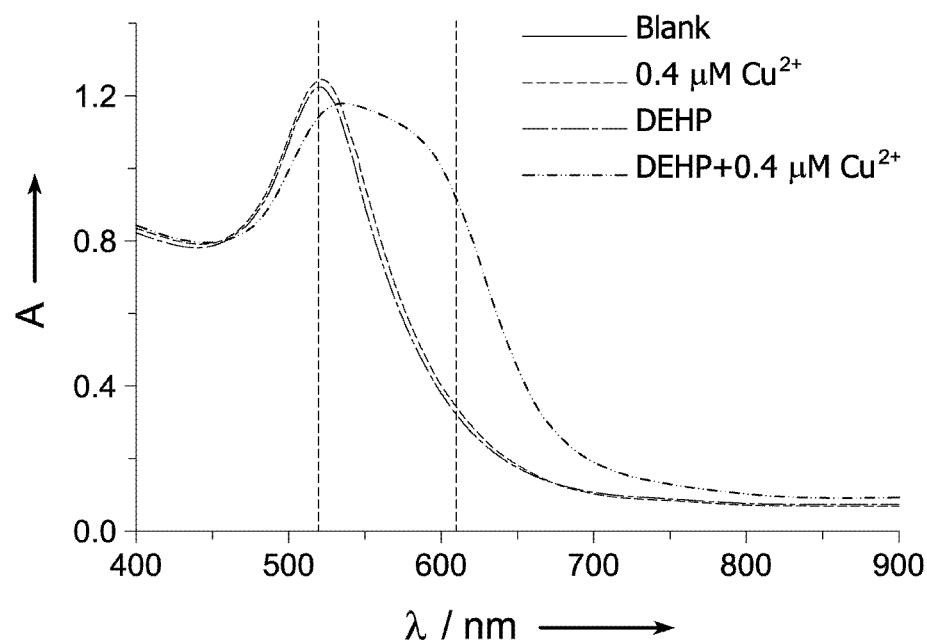
FIG. 4 are plots showing UV-vis absorbance of the UTP-AuNPs in solution upon addition of 10 g/L DEHP in the presence of (A) 0.4 µM, (B) 0.6 µM, (C) 0.8 µM, (D) 1 µM, and (E) 2 µM $Cu^{2+}$ acting as a cross-linker.
FIG. 4F is a histogram showing the absorption ratio $A_{610}/A_{520}$ of the UTP-AuNPs in solution upon addition of 10 g/L DEHP in the presence of various concentration of $Cu^{2+}$ indicated.
Figure 4B:
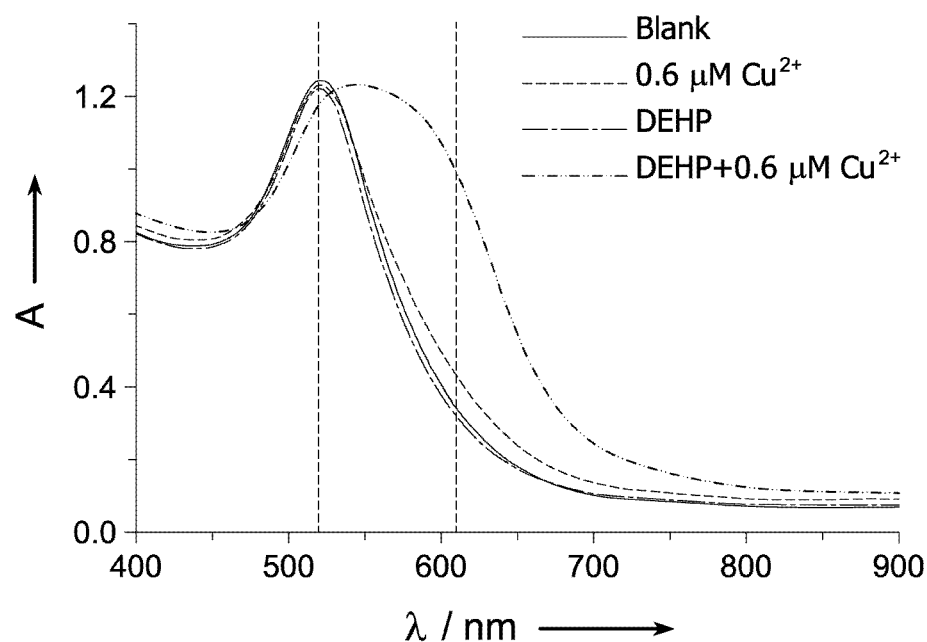
Figure 4C:
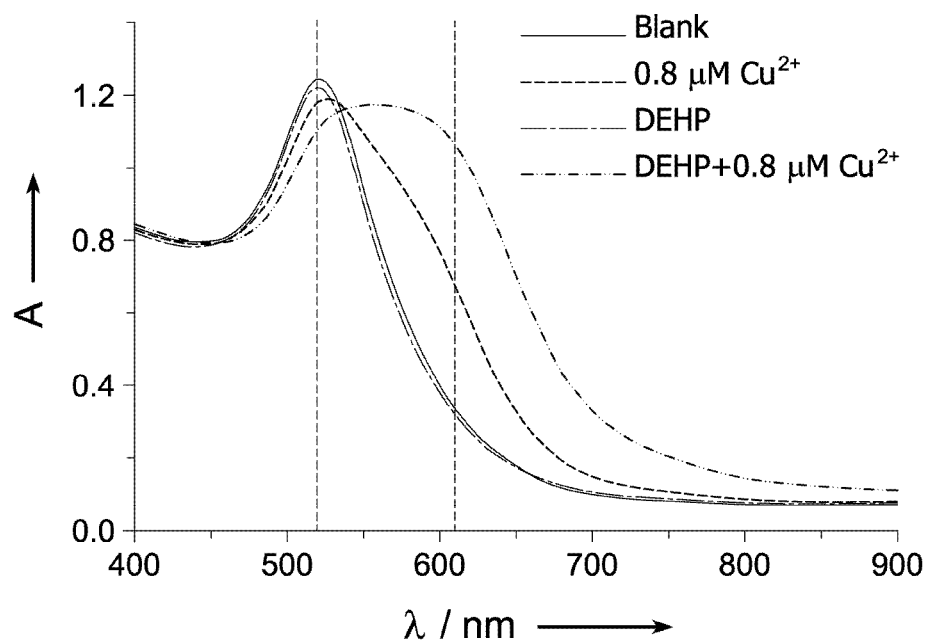
Figure 4D:
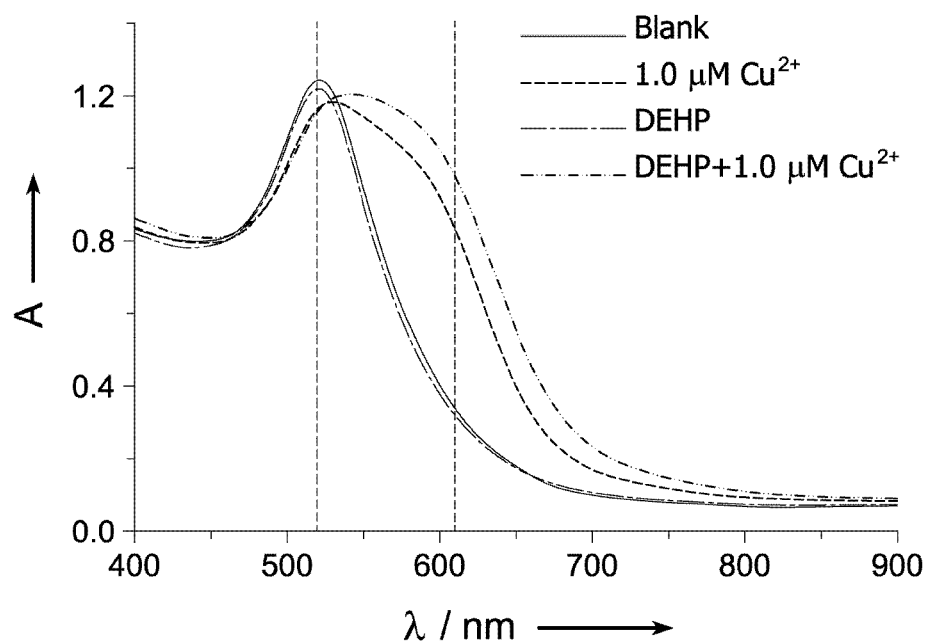
Figure 4E:
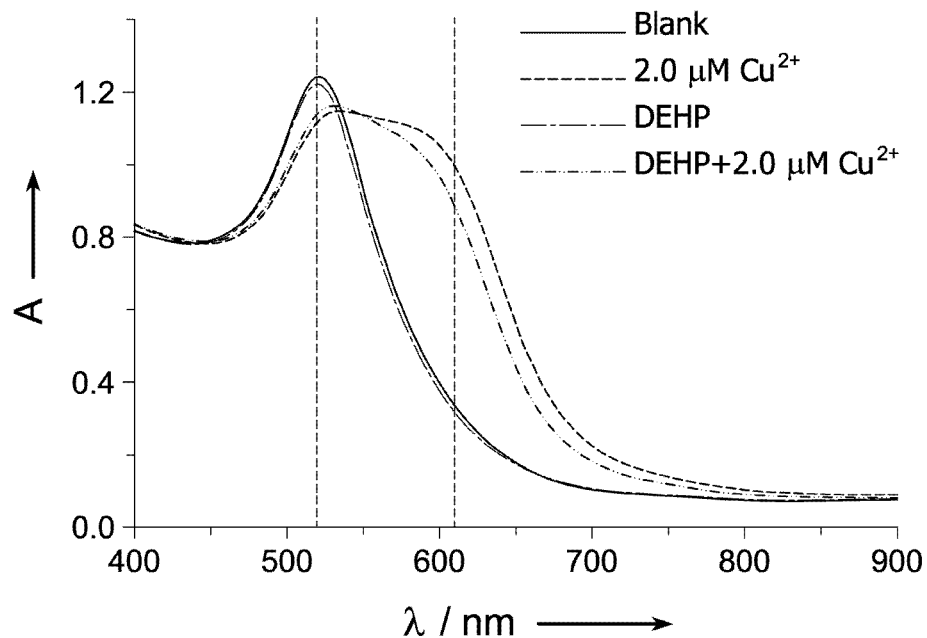
Figure 4F:
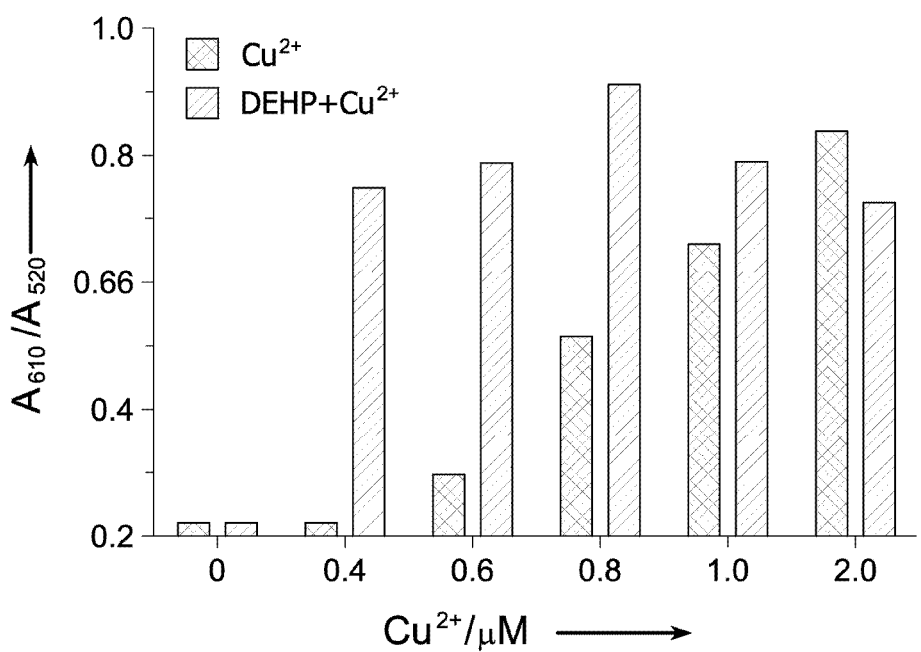
Figure 5A:
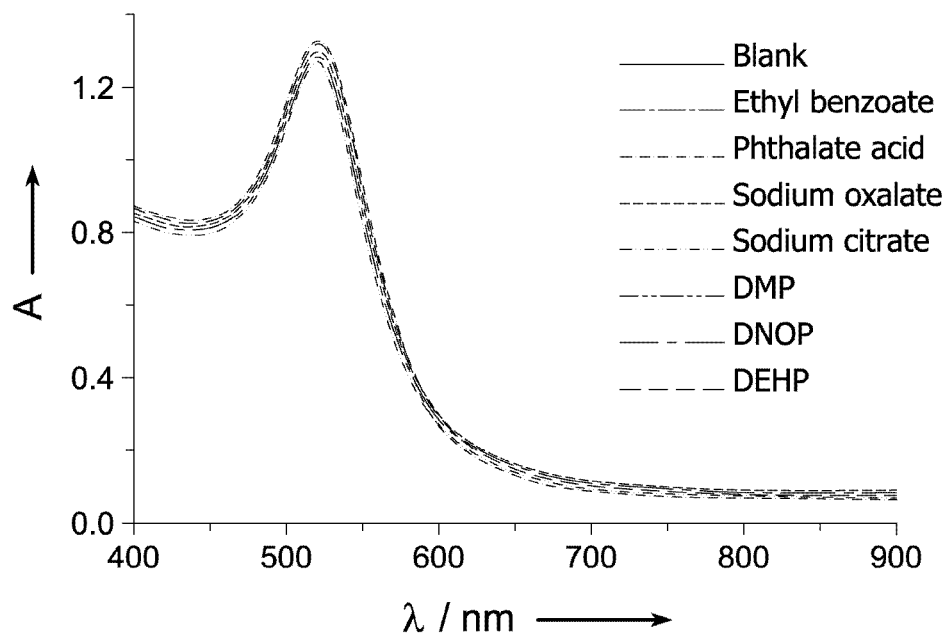
FIG. 5 are plots showing UV-vis absorbance of (A) ATP-modified AuNPs, (B) CTP-modified AuNPs, (C) GTP-modified AuNPs, and (D) UTP-modified AuNPs in solution upon addition of various phthalates including 10 g/L of DMP, DNOP and DEHP and certain control analytes including 10 g/L ethyl benzoate, phthalate acid, sodium oxalate and sodium citrate.
Figure 5B:
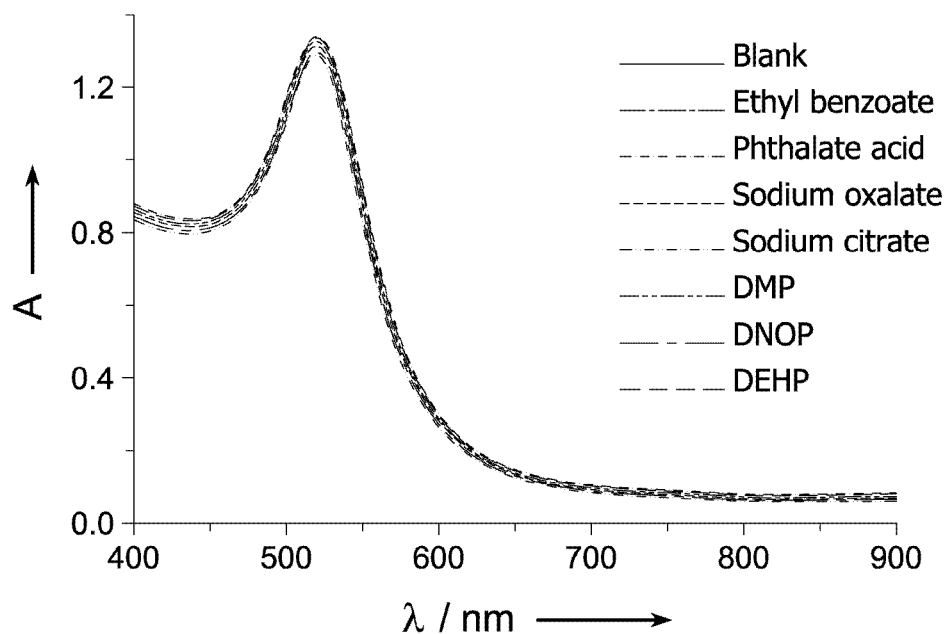
Figure 5C:
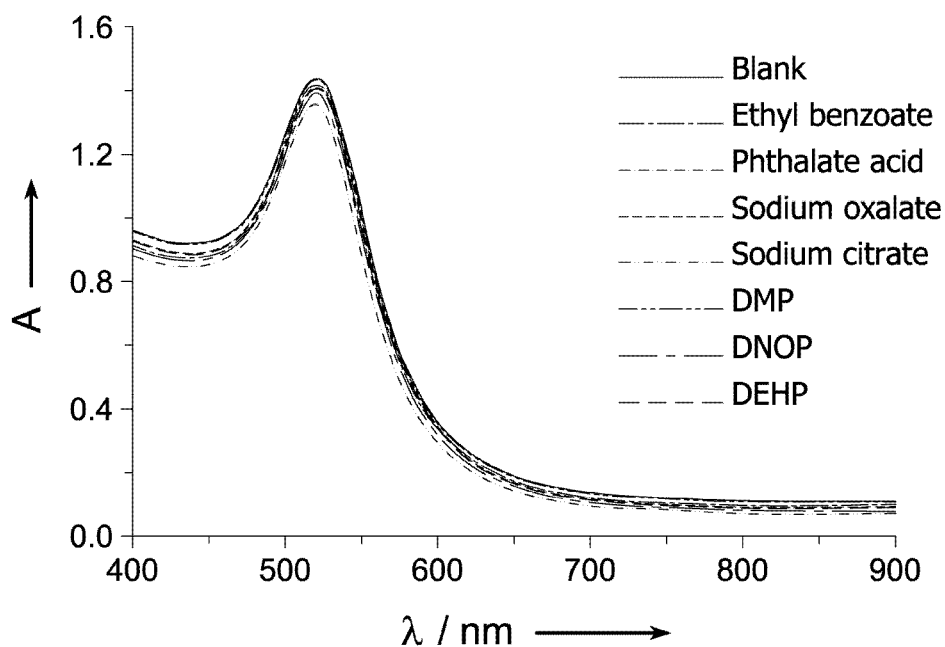
Figure 5D:
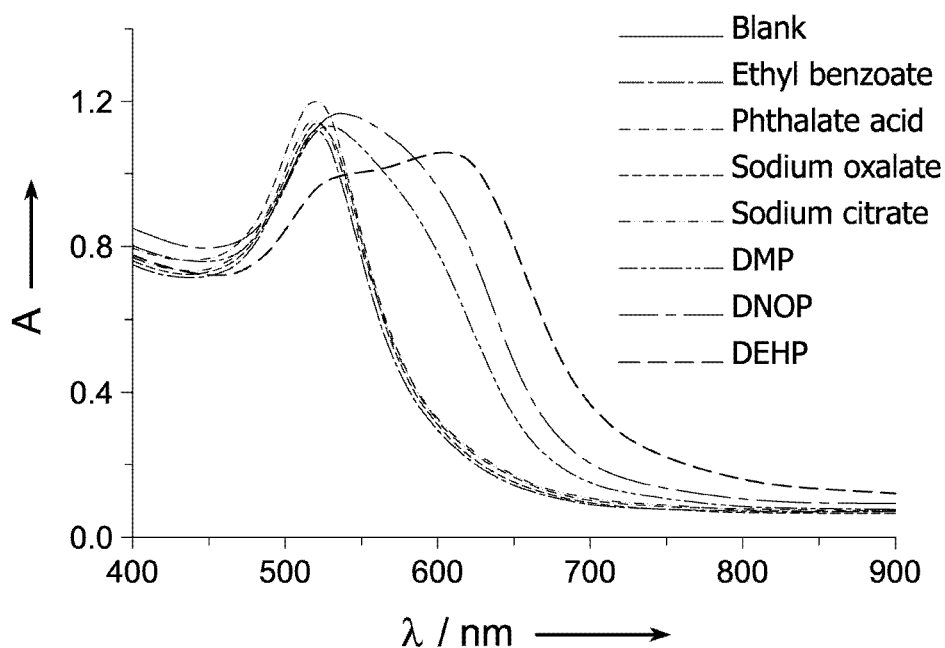
Figure 6A:
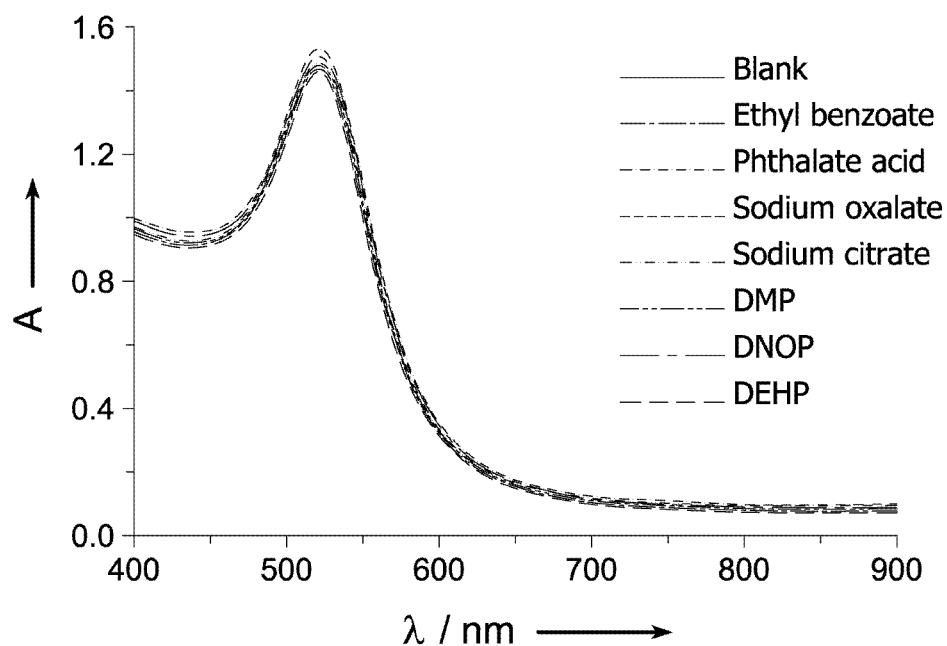
FIG. 6 are plots showing UV-vis absorbance of (A) dATP-modified AuNPs, (B) dCTP-modified AuNPs, (C) dGTP-modified AuNPs, and (D) dTTP-modified AuNPs in solution upon addition of various phthalates including 10 g/L of DMP, DNOP and DEHP and certain control analytes including 10 g/L ethyl benzoate, phthalate acid, sodium oxalate and sodium citrate.
Figure 6B:
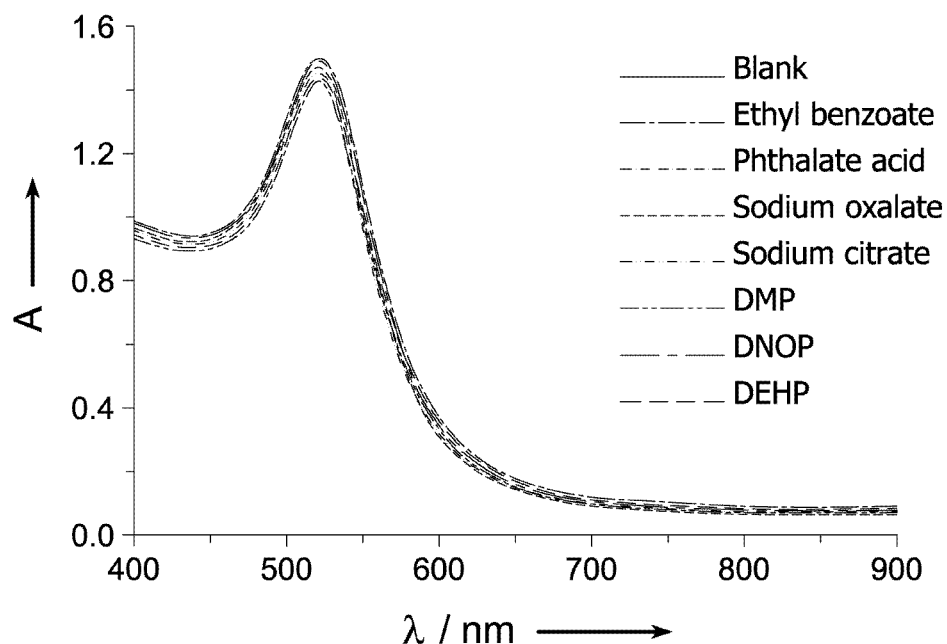
Figure 6C:
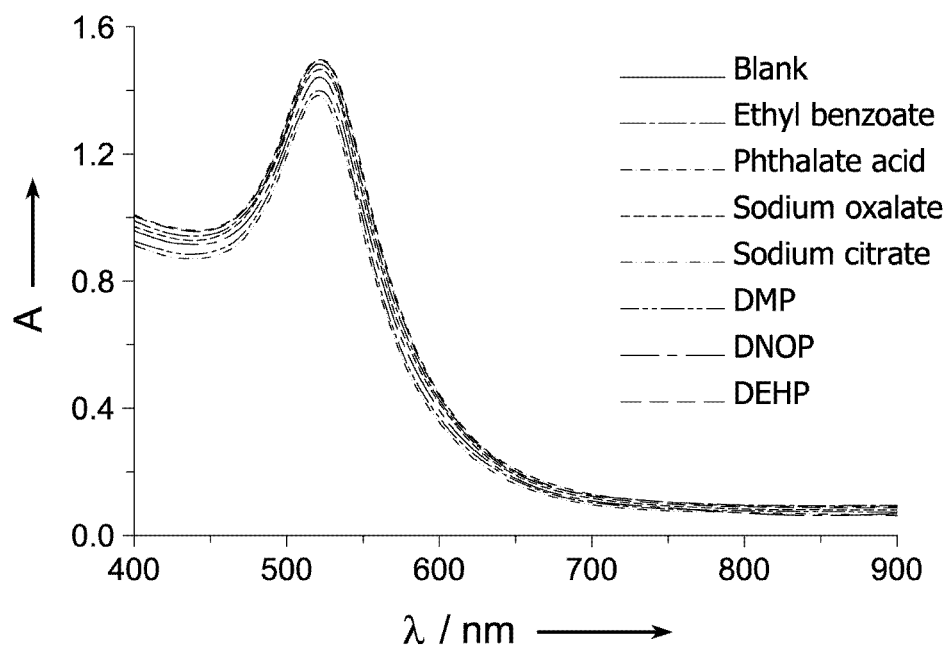
Figure 6D:
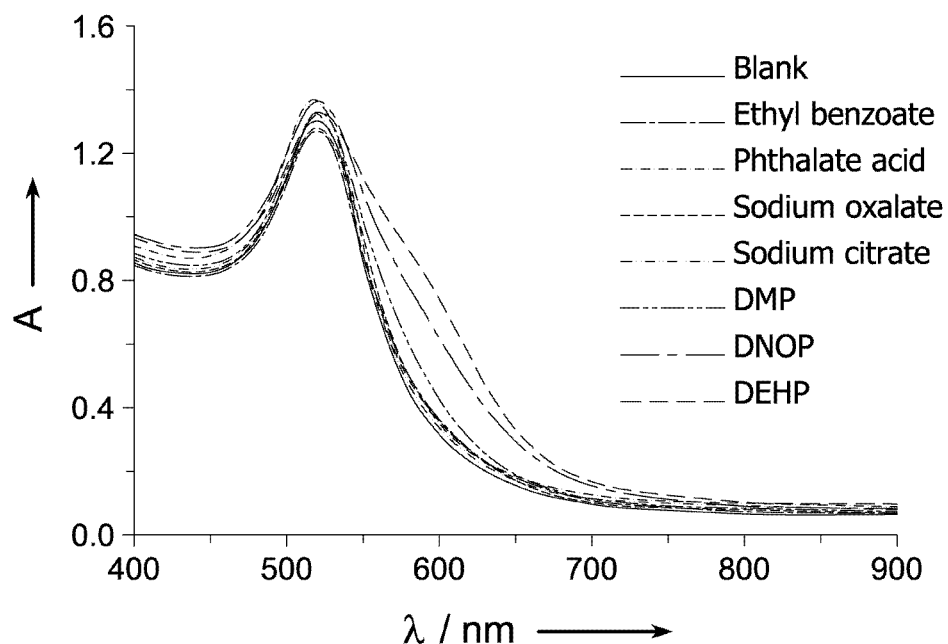

Transmission electron microscope (TEM) measurements of the UTP-AuNPs solution were performed on Jeol JEM-1230 instrument operated at an accelerating voltage of 80 kV. Samples for TEM studies were prepared by placing a drop of UTP-AuNPs solution on a copper grid. The films on the TEM grids were allowed to dry for 2 minutes following that extra solution was removed using a blotting paper. Photographs were taken with Nikon D3100 digital camera (Tokyo, Japan). As shown in the TEM images, UTP-AuNPs are highly dispersed in aqueous solution (FIG. 3C, image a), in the presence of $Cu^{2+}$ (FIG. 3C, image b), and in the presence phthalates (FIG. 3C, image c). The average size of the UTP-AuNPs was about 15 nm.

To obtain the absorption spectrum profile of the UTP-AuNPs solutions, the ultraviolet visible (UV-vis) absorption spectrum of the UTP-AuNPs solutions (with or without the presence of phthalates) were recorded with a microplate reader (BioTek Instruments, Winooski, Vt., USA) with wavelength ranging from 400 nm to 900 nm using a transparent 384-well microplate (Greiner, Germany). The resulting absorption spectrum profile is shown in FIG. 3A, further confirming that the U-AuNPs were highly stabilized against aggregation in the presence of 10 g/L phthalates dissolved in ethanol.

Example 3

Detection of Phthalates Using UTP-Modified AuNPs

UTP-modified gold nanoparticles (UTP-AuNPs) were prepared according to the procedure described in Example 1. The UTP-AuNPs were challenged to various concentrations of $Cu^{2+}$ in the absence or presence of di(2-ethyl-hexyl)phthalate (DEHP). The absorption ratio ($A_{610}/A_{520}$) of U-AuNPs was measured. The results are shown in FIG. 4A-F. The results indicate that absorption ratio ($A_{610}/A_{520}$) of U-AuNPs is sensitive to the concentrations of $Cu^{2+}$.

To determine the ability of UTP-modified AuNPs for detecting DEHP in 0.4 μM $Cu^{2+}$, colorimetric assays were carried out as follows: an aliquot of 50 μL mixed solution containing 10 μL 4 μM CuCl$_2$, 10 μL various concentration of DEHP dissolved in ethanol, 10 μL 10×NaNO$_3$-MOPS buffer (500 mM NaNO$_3$ and 200 mM 3-(4-morpholinyl)-1-propanesulfonic acid, pH 7.0) and 20 μL Mili-Q water was placed in the wells of a transparent 384-well microtiter plate. Then, 50 μL mononucleotides-modified AuNPs was added to the corresponding wells. Subsequently, the resulting solutions were incubated for 5 minutes before measuring their extinction spectra. The ultraviolet visible (UV-vis) absorption spectrum of the UTP-AuNPs solutions were recorded with a microplate reader (BioTek Instruments, Winooski, Vt., USA) with wavelength ranging from 400 nm to 900 nm using a transparent 384-well microplate (Greiner, Germany). The experiments of optimization of sensing conditions were carried out under identical conditions.

In the simultaneous presence of 0.4 μM Cu$^{2+}$ and 10 g/L phthalates, a significant absorption change of UTP-AuNPs was detected (as evidenced by an obvious decrease in the plasmon absorption at 520 nm and a strong increase in the surface plasmon band from 600-650 nm). Without being limited by any theory, it is believed that the simultaneous presence of phthalates and Cu$^{2+}$ allowed formation of a cross-network between UTP-AuNPs and phthalates, in which Cu$^{2+}$ act as a cross-linker, to induce the aggregation of UTP-AuNPs and resulted in the surface plasmon resonance (SPR) absorption band of UTP-AuNPs shifting to a longer wavelength, and consequently a color change from red to blue or purple (FIG. 3A-B). The phthalate-stimulated aggregation of U-AuNPs cross-linked by Cu$^{2+}$ was also verified by TEM image (FIG. 3A, image d).

Various metal ions, including 0.4 μM K$^+$, Ba$^{2+}$, Na$^+$, Mn$^{2+}$, Zn$^{2+}$, Fe$^{3+}$, Mg$^{2+}$, Ca$^{2+}$, were also tested as cross-linkers for detection of phthalates. KCl, BaCl$_2$, NaCl, MnCl$_2$, ZnCl$_2$, FeCl$_3$, MgCl$_2$, and CaCl$_2$ solutions were used to provide corresponding metal ions as cross-linkers. Each of the metal ions was examined under the same condition described above for 0.4 μM Cu$^{2+}$. As shown in FIG. 3A-B, the presence of Cu$^{2+}$ resulted in an obvious change in the $A_{610}/A_{520}$, of UTP-AuNPs upon addition of phthalates accompanied with appreciable color switch (from red to purple), while there was negligible changes in $A_{610}/A_{520}$ ratio and color upon addition of phthalates in the presence of other metal ions tested.

This example demonstrates that copper (II) ion can form coordination complexes with UTP and phthalates. Therefore, UTP-AuNPs can be used to detect phthalates in the presence of Cu$^{2+}$ through detecting the change in absorption ratio $A_{610}/A_{520}$ and/or color of the UTP-AuNP solution.

Example 4

Detection of Phthalates Using Various Nucleotide-Modified Gold Nanoparticles

Various nucleotide-modified gold nanoparticles (AuNPs) were prepared according to the procedure described in Example 1. The nucleotides that were used to modify AuNPs were ATP, GTP, CTP, dATP, dGTP, dCTP, and dTTP. The nucleotides' abilities in stabilizing AuNPs and allowing aggregation of AuNPs in the presence of Cu$^{2+}$ and various phthalates (DMP, DNOP and DEHP) were examined by measuring absorption spectrum profiles of the nucleotide-modified AuNPs. Several competing stimuli including ethyl benzoate, phthalate acid, sodium oxalate and sodium citrate were also used to determine the specificity of the nucleotide-modified AuNPs. The results are shown in FIGS. 5-6.

Figure 7:
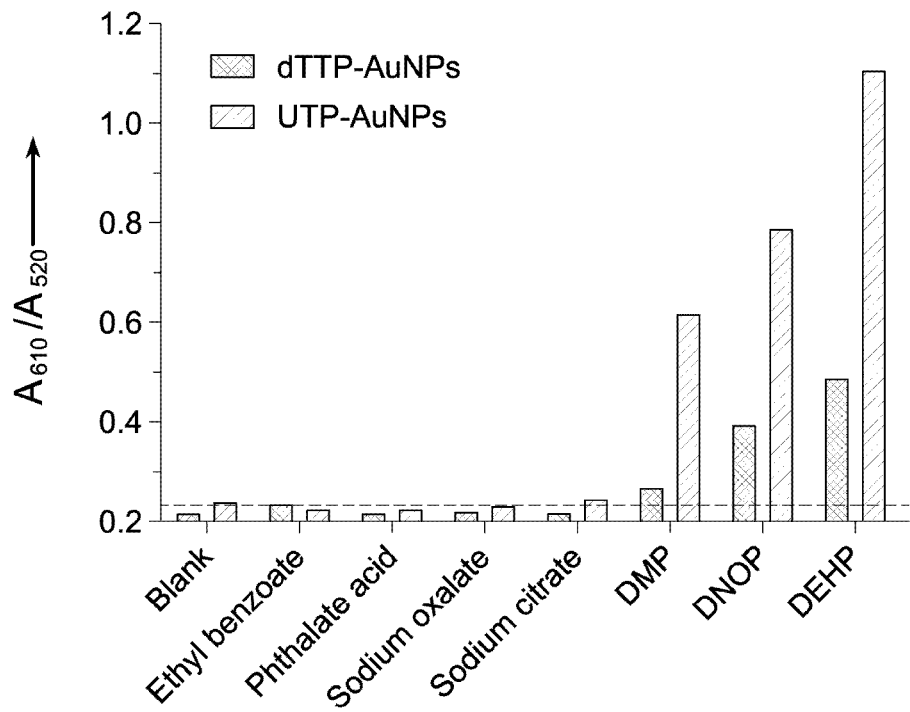
FIG. 7 is a histogram showing the $A_{610}/A_{520}$ absorption ratios of dTTP-modified AuNPs and UTP-modified AuNPs in solution upon addition of various phthalates including 10 g/L of DMP, DNOP and DEHP and certain control analytes including 10 g/L ethyl benzoate, phthalate acid, sodium oxalate and sodium citrate.

As shown in FIG. 5, UTP-AuNPs showed an appreciable higher $A_{610}/A_{520}$) for in the presence of all phthalates tested. dTTP-modified AuNPs (dTTP-AuNPs) displayed similar absorption properties toward phthalates as UTP-AuNPs, albeit displayed lower $A_{610}/A_{520}$) toward phthalates than that of U-AuNPs in the same condition (FIG. 6). Without being bound to any particular theory, it is believed that the similar responses by the UTP-modified AuNPs and the dTTP-modified AuNPs were results of their structure similarity. The comparison of the $A_{610}/A_{520}$ ratios of UTP-AuNPs and dTTP-AuNPs in the presence of various phthalates (DMP, DNOP and DEHP) and control analytes (ethyl benzoate, phthalate acid, sodium oxalate and sodium citrate) are shown in FIG. 7.

This example demonstrated that UTP-AuNPs and dTTP-AuNPs can selectively detect phthalates in a sample.

Example 5

Detection of di(2-ethylhexyl)phthalate (DEHP) Using U-AuNPs

Figure 8:
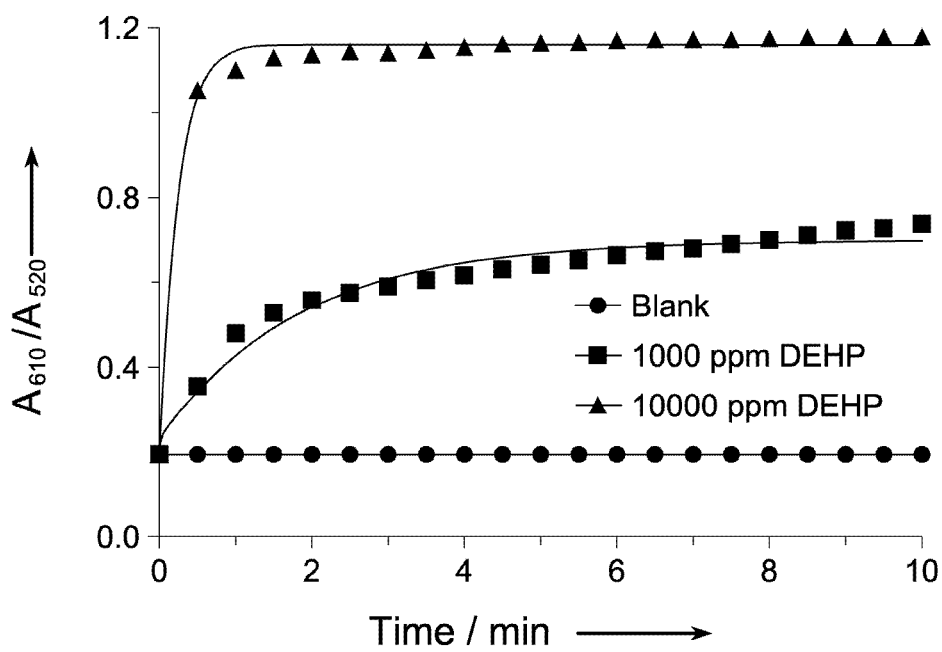
FIG. 8 is a plot showing time-course for the absorption ratio $A_{610}/A_{520}$ of UTP-modified AuNPs responding to DEHP in the presence of $Cu^{2+}$.

UTP-AuNPs were prepared according to the procedure described in Example 1. The UTP-AuNPs were challenged to DEHP in the presence of Cu$^{2+}$. The kinetic behaviors of absorption ratio ($A_{610}/A_{520}$) of UTP-AuNPs responding to 1000 ppm and 10000 ppm DEHP in the presence of 0.4 μM Cu$^{2+}$ was monitored, and the results are shown in FIG. 8. As shown in FIG. 8, the phthalate-stimulated aggregation of UTP-AuNPs in the presence of Cu$^{2+}$ was rapid, and the assay exhibited a nearly saturated signal within 5 minutes.

Figure 9A:
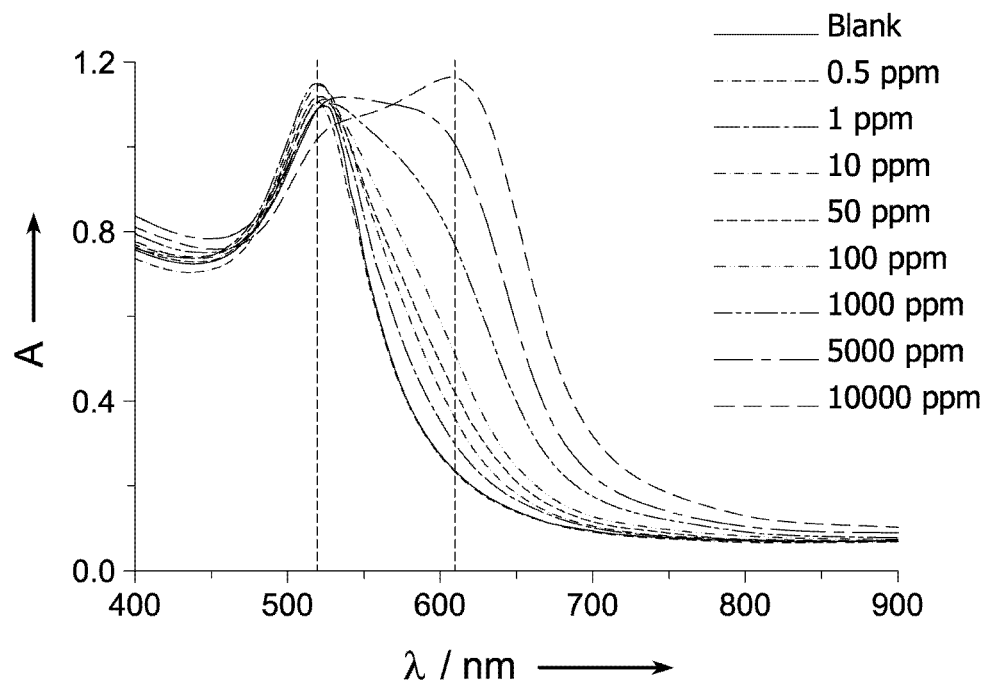
FIG. 9A shows the absorption spectra of the UTP-AuNPs in response to the various concentrations of DEHP indicated.

Then, UTP-AuNPs were used to detect DEHP with different concentrations (0, 0.5, 1, 10, 50, 100, 1000, 5000, and 10000 ppm) in the presence of 0.4 μM Cu$^{2+}$. As shown in FIG. 9A, with the increase in the concentration of DEHP, an obvious decrease in the absorption peak at 520 nm and an increase in the absorption peak from 600-650 nm were detected. These results were further confirmed by the observation that the color of the UTP-AuNPs gradually changed from initially red and finally to purple in response to the presence of DEHP.

Figure 9B:
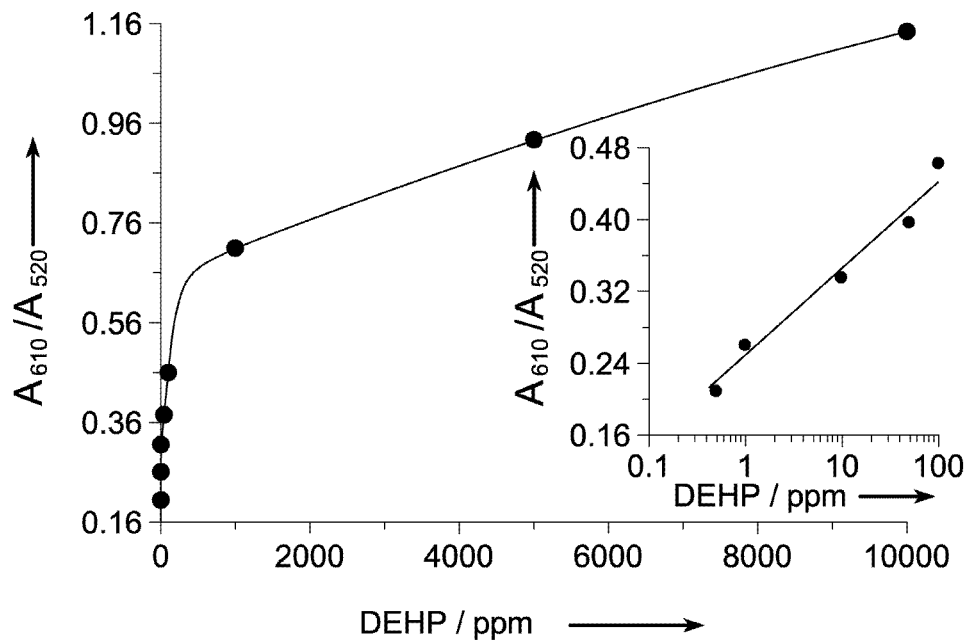
FIG. 9B is a plot of absorption ratios $A_{610}/A_{520}$ corresponding to the DEHP concentration in the range 0-10000 ppm in the presence of 0.4 µM $Cu^{2+}$. Inset: magnification of the plot of absorption ratios $A_{610}/A_{520}$ corresponding to the DEHP concentration in the range 0-100 ppm in the presence of 0.4 µM $Cu^{2+}$.

The sensitivity of the UTP-AuNPs probe for DEHP was further investigated. As shown in FIG. 9B, the absorption ratio ($A_{610}/A_{520}$) is sensitive to the concentration of DEHP. The $A_{610}/A_{520}$ absorption ratio ranges from 0.16 to 1.16 for DEHP with concentrations from 0.5 ppm to 10000 ppm. The results demonstrate that UTP-AuNPs can be used as a sensitive color indicator for detecting phthalates such as DEHP in the presence of cross-linker Cu$^{2+}$.

Example 6

Determination of Selectivity of U-AuNPs

UTP-AuNPs were prepared according to the procedure described in Example 1. The UTP-AuNPs were challenged to various analytes in the presence of 0.4 μM Cu$^{2+}$. The analytes used are dimethyl phthalate (DMP), di(n-octyl) phthalate (DNOP), DEHP, and some control analytes including ethyl benzoate, phthalate acid, sodium oxalate and sodium citrate. The UV-vis absorbance of the UTP-AuNPs in solutions upon addition of various analytes was determined according to the procedures described in Example 3. The absorption spectra of the UTP-AuNPs are shown in FIG. 10.

Figure 10A:
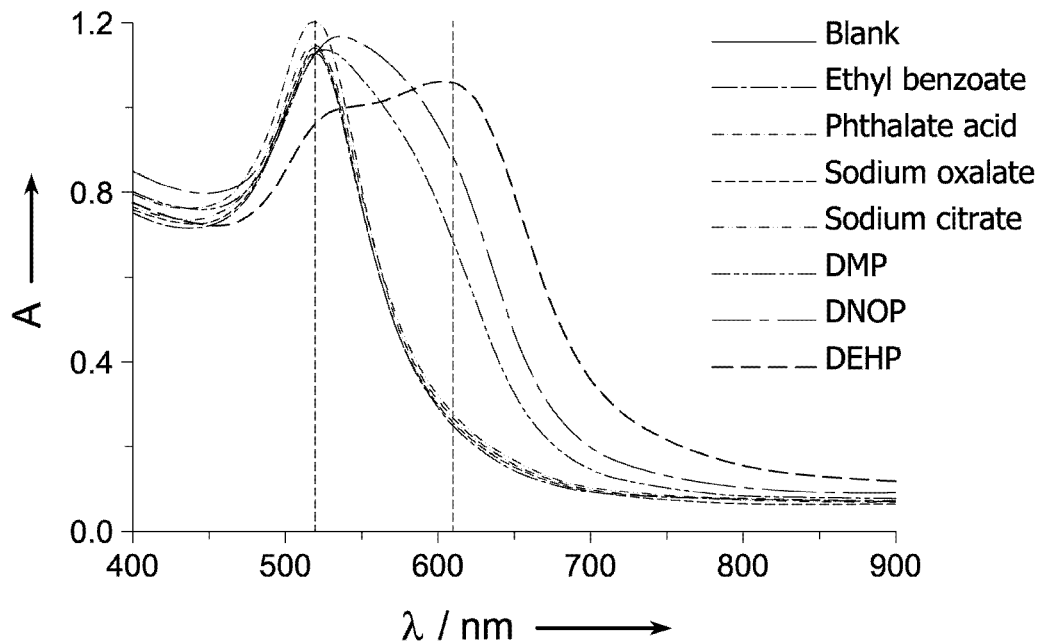
FIG. 10A shows the absorption spectra of the UTP-AuNPs in response to the various analytes indicated.
Figure 10B:
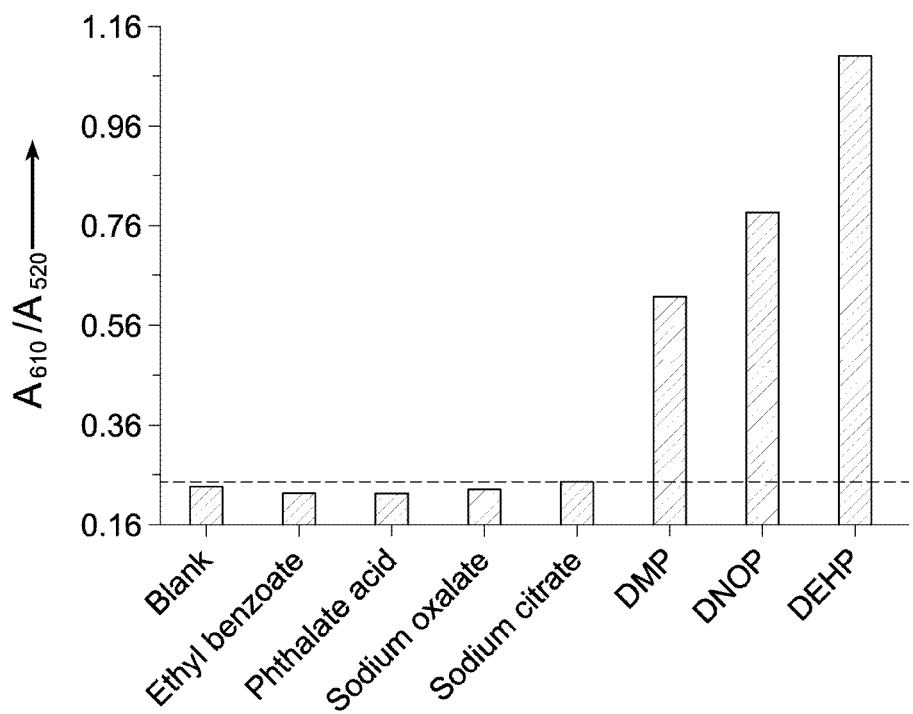
FIG. 10B is a plot of absorption ratios $A_{610}/A_{520}$ corresponding to the analytes indicated.

As shown in FIG. 10, the aggregation of UTP-AuNPs was selectively induced by phthalates in the presence of Cu$^{2+}$, and UTP-AuNPs exhibited excellent selectivity of phthalates as compared to other control analytes. Therefore, this example further demonstrates that UTP-AuNPs can be used as a simple, sensitive and reliable colorimetric probe for sensing various phthalates.

Example 7

Detection of Phthalates in Food Products Using UTP-AuNPs

UTP-AuNPs were prepared according to the procedure described in Example 1. Various food products including tea drinks, carbonated drinks, juice drinks and vegetable protein drinks were pretreated by adding DEHP to obtain test samples tainted with DEHP. Due to the extremely low pH of certain juice drinks, the pH value of the test samples were measured and adjusted to nearly neutral (i.e., about pH 7) using 10 M NaOH. The sarcocarp in certain drinks was centrifuged to precipitate (4000 rpm, 5 minutes). Then the supernatant was collected for phthalate-pretreatment and further colorimetric assay.

Figure 11A:
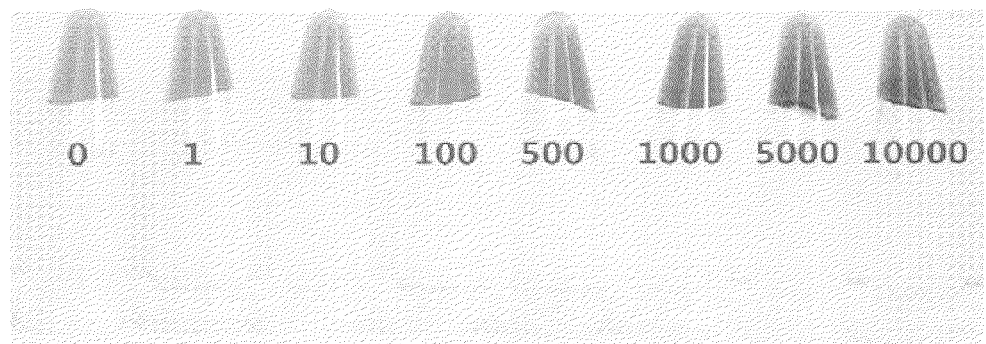
FIG. 11A shows visual color changes of the UTP-AuNPs sensor system without and with the addition of food samples tainted with 1, 10, 100, 500, 1000, 5000 and 10000 ppm DEHP.
Figure 11B:
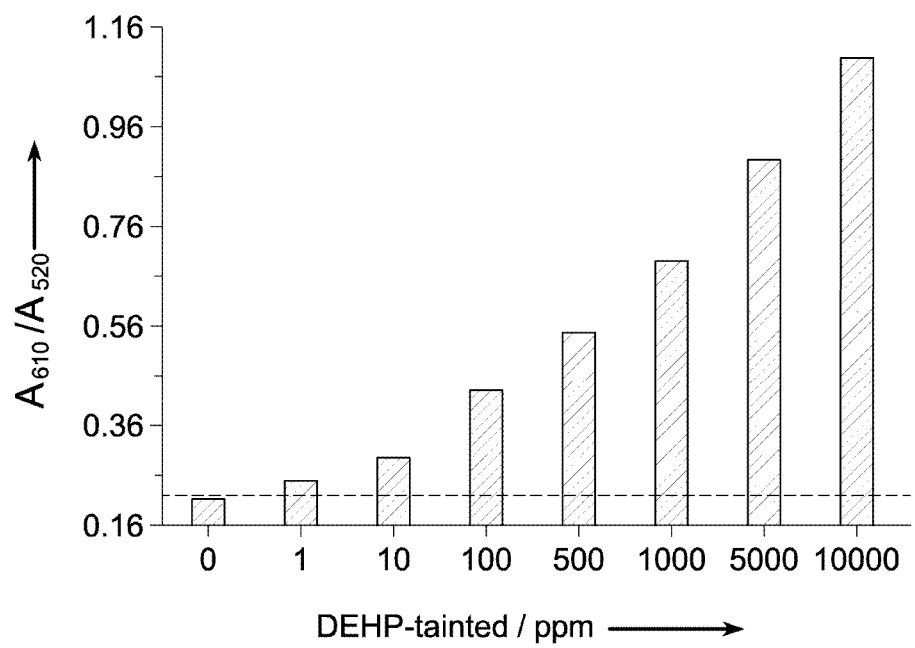
FIG. 11B is a plot of the corresponding absorption ratio $A_{610}/A_{520}$.

Colorimetric assays were conducted for each phthalate-tainted test sample according to the procedure described in Example 3. The addition of the food products without the phthalate-pretreatment did not lead to a distinguishable color change in the UTP-AuNPs solution. However, when the food samples tainted with 1, 10, 100, 500, 1000, 5000 and 10000 ppm DEHP were added to the sensor solution, respectively, a red-to-purple color change was observed (FIG. 11A), coinciding with the increasing absorption ratio $A_{610}/A_{520}$ demonstrated in FIG. 11B.

This example demonstrates that UTP-AuNPs can be used as a simple, sensitive and reliable colorimetric probe for sensing phthalates in food products.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

One skilled in the art will appreciate that, for this and other processes and methods disclosed herein, the functions performed in the processes and methods can be implemented in differing order. Furthermore, the outlined steps and operations are only provided as examples, and some of the steps and operations can be optional, combined into fewer steps and operations, or expanded into additional steps and operations without detracting from the essence of the disclosed embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A method for detecting a phthalate in a sample, the method comprising:
   providing a sample suspected of containing a phthalate;
   providing a plurality of nanoparticles having one or more attached sensing moieties, wherein the sensing moiety comprises one or more uridine 5'-triphosphate (UTP) groups, uridine 5'-diphosphate (UDP) groups, uridine monophosphate (UMP) groups, 2'-deoxythymidine 5'-triphosphate (dTTP) groups, 2'-deoxythymidine 5'-diphosphate (dTDP) groups, or deoxythymidine 5'-monophosphate (dTMP) groups;
   contacting the sample with the plurality of nanoparticles in the presence of a crosslinker to form a mixture, wherein the crosslinker is a copper (II) salt;
   maintaining the mixture under conditions to allow the crosslinker to bind the nanoparticles and any plasticizer present in the sample to form a nanoparticle aggregate; and
   detecting the nanoparticle aggregate, wherein the presence of the nanoparticle aggregate is indicative of the presence of a phthalate in the sample.

2. The method of claim 1, wherein the nanoparticles are metallic.

3. The method of claim 1, wherein the nanoparticles are gold nanoparticles, silver nanoparticles, platinum nanoparticles, aluminum nanoparticles, palladium nanoparticles, copper nanoparticles, cobalt nanoparticles, indium nanoparticles, nickel nanoparticles, or combinations thereof.

4. The method of claim 1, wherein the nanoparticles are gold nanoparticles, silver nanoparticles, quantum dots, carbon nanotubes, graphene oxides, or combinations thereof.

5. The method of claim 1, wherein the nanoparticles have an average diameter of about 12 nm to about 18 nm.

6. The method of claim 1, wherein the nanoparticles are present in the mixture at a concentration of about 1 nM to about 20 nM.

7. The method of claim 1, wherein the sensing moiety comprises one or more UTP groups or dTTP groups.

8. The method of claim 1, wherein the crosslinker is $CuCl_2$, $Cu(NO_3)_2$, $CuSO_4$, or combinations thereof.

9. The method of claim 1, wherein the crosslinker is present in the mixture at a concentration of about 0.2 μM to about 0.8 μM.

10. The method of claim 1, wherein the phthalate is di(2-ethyl-hexyl)phthalate (DEHP), dimethyl phthalate (DMP), di(n-octyl) phthalate (DNOP), diisononyl phthalate (DINP), or combinations thereof.

11. The method of claim 1, wherein the maintaining step is carried out for no more than 5 minutes.

12. The method of claim 1, wherein the maintaining step is carried out at a temperature of 10° C. to 40° C.

13. The method of claim 1, wherein formation of the nanoparticle aggregate results in a colorimetric change.

14. The method of claim 13, wherein the colorimetric change is correlated with the concentration of the phthalate in the sample.

15. The method of claim 1, wherein the detecting step comprises determining absorption ratio $A_{610}/A_{520}$ of the mixture.

16. The method of claim 1, wherein the detecting step is carried out by an optical sensor.

17. The method of claim 1, wherein the detecting step is carried out by visual observation of a user.

18. The method of claim 1, wherein the phthalate is present in the sample at a concentration of 0.05 ppM to 10000 ppM.

19. The method of claim 1, wherein the sample is a food product or a medicine product.

20. The method of claim 1, wherein the phthalate is di(2-ethylhexyl)phthalate (DEHP), diisononyl phthalate (DINP), di-n-butyl phthalate (DBP), benzyl butyl phthalate (BBP), diisodecyl phthalate (DIDP), di(n-octyl) phthalate (DNOP), diisooctyl phthalate (DIOP), diethyl phthalate (DEP), diisobutyl phthalate (DIBP), dimethyl phthalate (DMP), diallyl phthalate (DAP), di-n-propyl phthalate (DPP), butyl cyclohexyl phthalate (BCP), di-n-pentyl phthalate (DNPP), dicyclohexyl phthalate (DCP), di-n-hexyl phthalate (DNHP), diisohexyl phthalate (DIHxP), diisoheptyl phthalate (DIHpP), butyl decyl phthalate (BDP), n-Octyl n-decyl phthalate (ODP), di(2-Propyl Heptyl) phthalate (DPHP), diundecyl phthalate (DUP), diisoundecyl phthalate (DIUP), diisoundecyl phthalate (DTDP), diisotridecyl phthalate (DIUP), or a combination thereof.

* * * * *

UNITED STATES PATENT AND TRADEMARK OFFICE
CERTIFICATE OF CORRECTION

PATENT NO. : 8,822,384 B2
APPLICATION NO. : 13/814610
DATED : September 2, 2014
INVENTOR(S) : Ye et al.

Page 1 of 1

It is certified that error appears in the above-identified patent and that said Letters Patent is hereby corrected as shown below:

On the Title Page, item (56), under "OTHER PUBLICATIONS", in Column 2, Line 2, delete "Siliver" and insert -- Silver --, therefor.

On the Title Page, item (56), under "OTHER PUBLICATIONS", in Column 2, Line 8, delete "Bis-Phenathroline" and insert -- Bis-Phenanthroline --, therefor.

On the Title Page, item (56), under "OTHER PUBLICATIONS", in Column 2, Lines 35-38, delete "Kellett, et al., Bis-phenanthroline copper (II) phthalate complexes are potent in vitro antitumour agents with 'self-activating' metallo-nuclease and DNA binding properties, Dalton Trans., 40:1024 (2011).".

On Title Page 2, item (56), under "OTHER PUBLICATIONS", in Column 1, Lines 9-12, delete "Lomozik & Jastrzab, Non-covalent and coordination interactions in Cu(II) systems with uridine, uridine 5'-monophosphate and triamine or tetramine as biogenic amine analogues in aqueous solutions, J. Inorg. Biochem., 97:179 (2003).".

Signed and Sealed this
Tenth Day of March, 2015

Michelle K. Lee
*Deputy Director of the United States Patent and Trademark Office*